(12) United States Patent
Sugiyama et al.

(10) Patent No.: US 7,842,019 B2
(45) Date of Patent: Nov. 30, 2010

(54) ABSORBENT PRODUCT

(75) Inventors: Katsuhiko Sugiyama, Kasugai (JP); Yoshiaki Takamatsu, Tokyo (JP); Rie Kuwabara, Tokyo (JP); Masaru Tsubata, Kasugai (JP); Migaku Suzuki, Tokyo (JP)

(73) Assignees: Oji Paper Co., Ltd., Tokyo (JP); Japan Absorbent Technology Institute, Tokyo (JP)

( * ) Notice: Subject to any disclaimer, the term of this patent is extended or adjusted under 35 U.S.C. 154(b) by 0 days.

(21) Appl. No.: 11/930,710

(22) Filed: Oct. 31, 2007

(65) Prior Publication Data

US 2008/0065038 A1 Mar. 13, 2008

Related U.S. Application Data

(62) Division of application No. 10/311,653, filed as application No. PCT/JP01/05584 on Jun. 28, 2001.

(30) Foreign Application Priority Data

| Jun. 29, 2000 | (JP) | ............................... 2000-197378 |
| Nov. 14, 2000 | (JP) | ............................... 2000-346949 |
| Jan. 10, 2001 | (JP) | ............................... 2001-002945 |

(51) Int. Cl.
A61F 13/15 (2006.01)
A61F 13/20 (2006.01)

(52) U.S. Cl. .......................... 604/385.01; 604/385.101; 604/385.16

(58) Field of Classification Search ................. 604/367, 604/378, 380, 385.01, 385.16, 385.22, 387, 604/396

See application file for complete search history.

(56) References Cited

U.S. PATENT DOCUMENTS

| 5,873,868 | A | 2/1999 | Nakahata |
| 5,891,124 | A | 4/1999 | Nomura et al. |
| 5,928,211 | A | 7/1999 | Gustafsson et al. |
| 5,947,947 | A | 9/1999 | Tanzer et al. |
| 6,790,202 | B2 * | 9/2004 | Klemp et al. .......... 604/385.01 |
| 6,794,557 | B1 * | 9/2004 | Klemp et al. ............... 604/378 |

FOREIGN PATENT DOCUMENTS

| EP | 0 908 162 A | 4/1999 |
| EP | 0 962 207 A | 12/1999 |

(Continued)

OTHER PUBLICATIONS

Office Action issued by JPO for Japanese Patent Appln. 2001-002945 dated Nov. 27, 2007. Two pages. English translation of areas marked on Japanese version (1 page).

(Continued)

*Primary Examiner*—Michele Kidwell
(74) *Attorney, Agent, or Firm*—Frommer Lawrence & Haug LLP; Ronald R. Santucci

(57) ABSTRACT

In an absorbent product such as a diaper comprising a back sheet, an absorber, and a skin contact sheet, the skin contact sheet is disposed on the absorber as the uppermost layer which comes in contact with the skin of the wearer and has openings which allow the passage of excretions. The absorber and the skin contact sheet are joined only at both ends of the absorbent product in the longitudinal directions.

3 Claims, 30 Drawing Sheets

FOREIGN PATENT DOCUMENTS

| | | |
|---|---|---|
| JP | 01-162806 A | 6/1989 |
| JP | 02-065861 A | 3/1990 |
| JP | 02-501977 A | 7/1990 |
| JP | 2-297364 A | 12/1990 |
| JP | 3-202057 A | 9/1991 |
| JP | 03-202057 A | 9/1991 |
| JP | 5-35126 | 5/1993 |
| JP | 05-305109 A | 11/1993 |
| JP | 6-9621 | 2/1994 |
| JP | 6-11723 | 2/1994 |
| JP | 06-327715 A | 11/1994 |
| JP | 09-276333 A | 10/1997 |
| JP | 10-014976 A | 1/1998 |
| JP | 10-043236 A | 2/1998 |
| JP | 10-168230 | 6/1998 |
| JP | 10-168230 A | 6/1998 |
| JP | 10-314226 A | 12/1998 |
| JP | 11-253490 A | 9/1999 |
| JP | 2000-508933 | 7/2000 |
| WO | WO 88/05269 A | 7/1988 |
| WO | WO 97/39710 A | 10/1997 |

OTHER PUBLICATIONS

Office Action issued by JPO for Japanese Patent Appln. 2000-197378 dated Jun. 19, 2009. Three pages. English translation of areas marked on Japanese version (3 pages).

Office Action issued by JPO for Japanese Patent Appln. 2000-346949 dated Jun. 23, 2009. Three pages. English translation of areas marked on Japanese version (3 pages).

\* cited by examiner

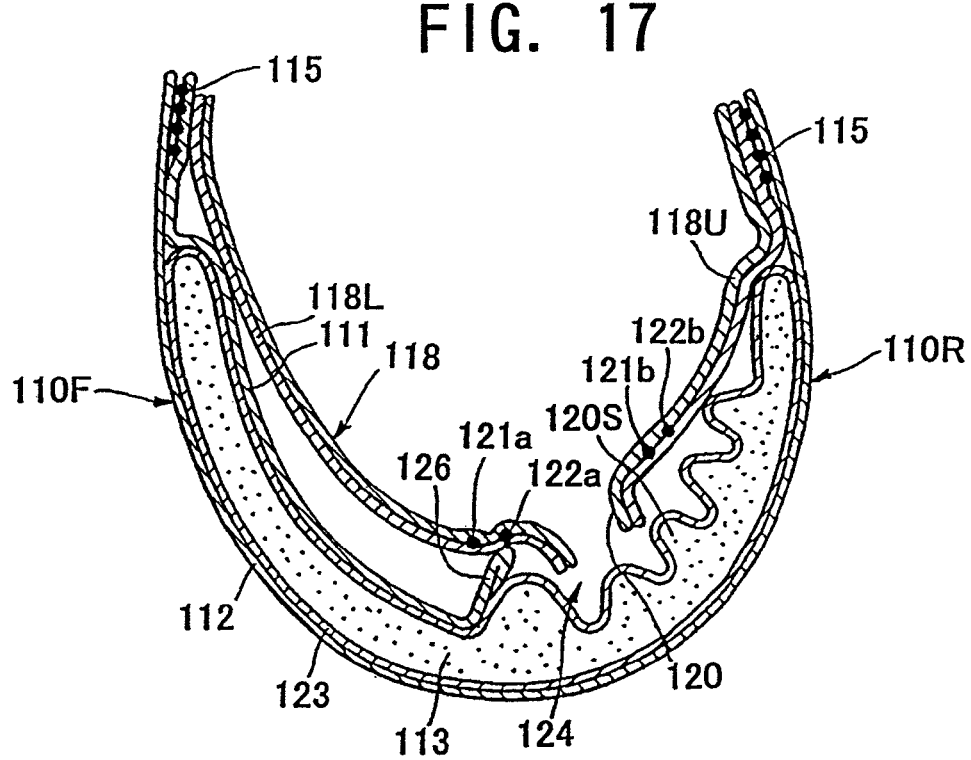
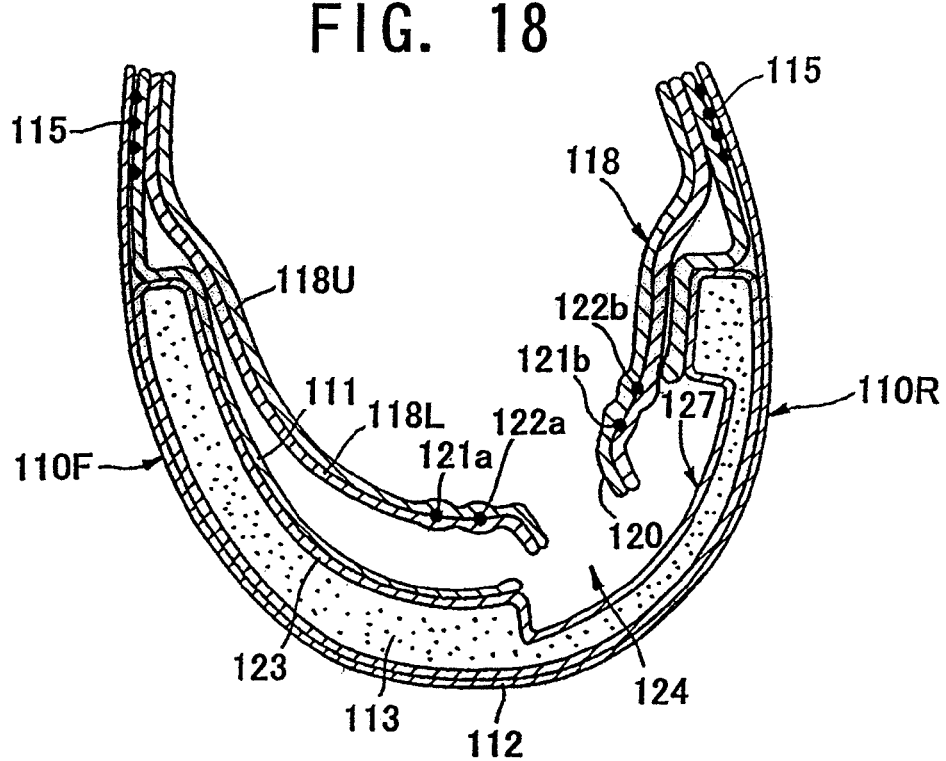

ABSORBENT PRODUCT

CROSS-REFERENCE TO RELATED APPLICATIONS

This application is a division of U.S. patent application Ser. No. 10/311,653 filed Dec. 17, 2002 entitled "Absorbent Product" which is a 371 filing of International Application No. PCT/JP01/05584 filed Jun. 28, 2001 which claims priority benefits of Japanese Patent Application No. 2000-197378 filed Jun. 29, 2000 and Japanese Patent Application No. 2000-346949 filed Nov. 14, 2000 and Japanese Patent Application No. 2001-2945 filed Jan. 10, 2001, the disclosures of which are hereby incorporated by reference.

TECHNICAL FIELD

The present invention relates to absorbent products such as a diaper. For details, the present invention relates to an absorbent product considered and designed so that stool is prevented from being directly attached to a wearer's backside and skin troubles of the backside are decreased.

BACKGROUND ART

Concerning causes and development mechanism of diaper rash, according to "So-Called Diaper Rash" of Kazuya YAMAMOTO described in pages 949 to 956 (1998) of "Clinical of Dermatology" Vol. 30, authored by Kazuya YAMAMOTO, issued by Kinbara Shuppan, (1) ammonia is generated, when urine and stool are mixed, (2) this ammonia sets environment to be alkaline, (3) an enzyme in the stool is strongly activated in an alkaline atmosphere and a weak portion of skin is inflamed by the enzyme and ammonia, and the diaper rash is generated. As a cause for producing the weak portion of the skin, a mechanical stimulus such as touch of a diaper constituting material in contact with the skin, an environment inside the diaper in which the skin is in a puckered state because of high humidity in the diaper, and the like are pointed out.

By capability enhancement with the technical progress of a super absorbent polymer (SAP) against the causes of the above-described diaper rash, for example, discharged urine is quickly absorbed and permeation/diffusion of the urine is minimized. Thereby, it is possible to prevent the urine from being easily mixed with the discharged stool. Moreover, concerning the environment inside the diaper, for example, when an air-permeable sheet is used in the diaper, a countermeasure against a sweaty skin in the diaper is possible, and the skin is effectively prevented from being puckered. With this advancement of the countermeasure against the diaper rash, skin troubles have decreased such as rash generated by use of a so-called disposable diaper.

However, countermeasures have not been sufficient yet for prevention of rash by substantially simultaneously discharged urine and stool, or soft stool. Even when the soft stool is not mixed with the urine, the stool left to stand is a heavy burden on the skin. Since the soft stool hardly passes through a top sheet of the diaper abutting on the skin, a part of moisture shifts to an absorber, but the remaining part remains in the top sheet and sticks to a backside of a wearer. Therefore, even when a trouble is not generated in the skin, a wiping operation of the backside becomes laborious at a time of diaper changing.

To prevent the above-described mixing of the stool and urine or the sticking of the stool to the backside, a diaper which can separate the urine and stool is proposed, for example, in Jpn. Pat. Appln. KOKAI Publication No. 61-41304, Jpn. UM Appln. KOKAI Publication Nos. 6-5614, 6-21623, 6-11723, and Jpn. Pat. Appln. KOKAI Publication No. 10-192339.

In the diaper disclosed in the Jpn. Pat. Appln. KOKAI Publication No. 61-41304, an opening long in a longitudinal direction is disposed in the middle of the top sheet, an elastic member is attached to a peripheral edge of the opening, and arrangements are made such that so-called sturdiness is imparted to the top sheet and the opening is prevented from being closed. Moreover, the diaper disclosed in the Jpn. UM Appln. KOKAI Publication No. 6-5614 includes: a concave portion extending under the opening disposed in a surface sheet; and a valve portion constituted by the surface sheet extended into a middle portion from the periphery of the opening. Arrangements are made such that the stool separated by the opening is prevented from returning. For the diaper disclosed in the Jpn. UM Appln. KOKAI Publication No. 6-21623, two sets of flaps extending in longitudinal and width directions are overlapped with each other, and the opening is formed in the middle of the overlap, so that the area of the opening containing the stool can be set to be large. Furthermore, the diaper disclosed in the Jpn. UM Appln. KOKAI Publication No. 6-11723 includes: a second surface sheet disposed on a first surface sheet; and further a plurality of elastic members for expanding the opening disposed in the middle portion of the second surface sheet in the longitudinal direction in a transverse direction. In the diaper disclosed in the Jpn. Pat. Appln. KOKAI Publication No. 10-192339, a spacer is disposed between the absorber and top sheet, and the opening connected to a space formed by the spacer is formed in the top sheet.

For the diapers disclosed in the Jpn. Pat. Appln. KOKAI Publication No. 61-41304 and Jpn. UM Appln. KOKAI Publication No 6-5614, when actual wearing of the diaper is observed, a crotch region of the diaper is attracted toward the middle by a wearer's legs thigh. It has further been found that the region hangs downwards without closely sticking to the skin. That is, since the crotch region of the top sheet or surface sheet (hereinafter these will be generically referred to as the top sheets) of each of these diapers does not closely stick to a wearer's crotch, the opening disposed in the top sheet does not have any meaning. This causes a disadvantage that the stool spreads over the top sheet. Even if the position of the opening of the top sheet agrees with that of wearer's anus, the top sheet does not closely stick to the wearer's crotch, and the opening is therefore in a closed state. Therefore, it is expected that the stool cannot be guided between the top sheet and a back sheet via the opening.

Moreover, with the diaper disclosed in the Jpn. UM Appln. KOKAI Publication No. 6-21623, when the area of the opening formed in the second surface sheet is set to be large, the position of the opening can substantially securely be aligned with that of the wearer's anus. Conversely, the opening area of the opening is excessively large, the stool is guided between the second surface sheet and first surface sheet via the opening and returns again onto the second surface sheet via the opening, and the wearer's backside may be made dirty in high possibility.

Furthermore, for the diaper disclosed in the Jpn. UM Appln. KOKAI Publication No 6-11723, the opening is expanded only in the width direction, the opening is collapsed by the wearer's crotch, and the sufficient function of the opening cannot basically be fulfilled in the same manner as in the prior art.

In the diaper disclosed in the Jpn. Pat. Appln. KOKAI Publication No. 10-192339, since the space for containing the stool is formed between the absorber and top sheet by the spacer using the elastic material, the spacer is in contact with the wearer's backside via the top sheet. There is a disadvantage that comfort of wear is impaired. Moreover, occupancy of the opening formed in the top sheet is small. Therefore, stool having low fluidity cannot easily pass through the opening of the top sheet quickly, and the wearer's backside may be made dirty.

DISCLOSURE OF INVENTION

An object of the present invention is to provide absorbent products such as a diaper in which a skin contact sheet including at least one opening can be used to decrease skin troubles such as diaper rash.

According to one aspect of the present invention, there is provided an absorbent product comprising: a portion which is constituted of a liquid-impervious back sheet and an absorber superposed upon the back sheet and which extends to a back body portion positioned on a back side from a front body portion positioned on a front side of a wearer in a wearing state, wherein a skin contact sheet as an uppermost layer in contact with a skin of the wearer is disposed on the absorbent product, the skin contact sheet includes at least one opening to allow passage of excretions from the wearer, and the absorbent product and skin contact sheet are joined to each other in opposite ends in a longitudinal direction of the absorbent product, and are kept in a non-contact state so that a gap can be formed between the absorbent product and skin contact sheet in portions other than the opposite ends.

Examples of a preferred mode in which the absorbent product of the present invention is to be achieved are as follows.

The absorbent product includes a liquid-pervious top sheet with which the absorber is covered and which is disposed between the absorber and skin contact sheet, and the top sheet is in a contact joined state with the skin contact sheet in the opposite ends of the longitudinal direction of the absorbent product, and is kept in a non-contact state so that the gap can be formed between the top sheet and skin contact sheet in the portions other than the opposite ends.

The skin contact sheet is disposed in a portion extending to a back body region from at least a crotch region of the absorbent product in the wearing state of the absorbent product.

The skin contact sheet is disposed in a portion extending to a back body region from a front body region of the absorbent product in the wearing state of the absorbent product, and includes a cutout portion in a middle portion of the front body region in a width direction in the wearing state of the absorbent product.

The skin contact sheet is constituted, for example, of a mesh material, foamed resin, elastic member, and the like.

The absorber is disposed in at least the front body region.

The absorbent product further includes an elastic member joined to the skin contact sheet in an extended state so as to surround the opening formed in the skin contact sheet.

The absorbent product further includes at least four elastic members joined to the skin contact sheet in an extended state so as to surround the opening formed in the skin contact sheet, and the elastic members are arranged so as to extend to the back body region from the front body region of the absorbent product and to pass in the vicinity of the opening.

The absorbent product further includes elastic members arranged in a crossed mode in the skin contact sheet so as to surround the opening of the skin contact sheet and to intersect with each other.

The absorbent product further includes
at least two elastic members extending to reach one side edge of the back body region from one side edge of the front body region through opposite side edges of the opening of the skin contact sheet, and
at least two elastic members extending to reach the other side edge of the back body region from the other side edge of the front body region of the absorbent product through the opposite side edges of the opening of the skin contact sheet.

The absorbent product further includes
at least two elastic members extending from one side edge of the front body region to the other side edge of the front body region through opposite side edges of the opening and crotch region, and
at least two elastic members extending from one side edge of the back body region of the absorbent product to the other side edge of the back body region through the opposite side edges of the opening and crotch region.

The elastic members are arranged in such a manner that a tensile force acts substantially uniformly in mutual approach directions of edges of the opening disposed opposite to each other.

In a portion corresponding to the front body region, a cutout portion is formed in a middle portion of the skin contact sheet in a width direction.

The skin contact sheet includes a liquid-impervious portion.

In a portion corresponding to the front body region, a second absorber is disposed in the skin contact sheet.

The back sheet forms a pair of longitudinal side flaps with which a waist part of the wearer is covered.

Furthermore, opposite edges of the respective side flaps are joined to or overlapped with each other to form a waist surrounding opening and a pair of leg surrounding openings.

Additionally, the absorbent product further includes a stretchable band member with which a waist of the wearer is surrounded, the skin contact sheet is connected to the stretchable band member at the ends of the skin contact sheet in a longitudinal direction, and thereby the skin contact sheet can elastically be displaced with respect to a body of the wearer in an appropriate range.

The stretchable band member is constituted of front and back end flaps which have stretchable properties,
the skin contact sheet is joined to the respective end flaps at opposite ends of the sheet in the longitudinal direction, and
a dimension of the skin contact sheet between the end flaps in the longitudinal direction is set to be shorter than an extension dimension between the end flaps.

The opening of the skin contact sheet is a cutout portion.

The skin contact sheet includes a cutout portion formed in a middle portion of the front body region in the width direction, and an opening formed in the crotch region.

The end flap is formed by turning back the back sheet on the absorber.

The end flap includes a stretchable elastic member which is disposed along the waist surrounding opening and which has a length to obtain an extended state in the wearing state.

The stretchable band member includes a pair of front and back slits formed along the waist surrounding opening, and elastic members attached to positions disposed opposite to each other via each slit so as to obtain an extended state in the wearing state.

The opposite ends of the skin contact sheet in the longitudinal direction are joined to the stretchable elastic band member in the vicinity of the pair of slits, and a dimension of the skin contact sheet positioned between the pair of slits in the longitudinal direction is set to be shorter than an extension dimension between the pair of slits.

The opening of the skin contact sheet is a cutout portion.

The opposite ends of the skin contact sheet in the longitudinal direction are joined to the elastic band member in the vicinity of the pair of slits, a cutout portion is formed in a middle portion of the front body region of the skin contact sheet in the width direction, an opening is formed in the crotch region, and a longitudinal dimension of the skin contact sheet positioned between the pair of slits is set to be shorter than an extension dimension between the pair of slits.

At least one of opposite ends of the skin contact sheet in the longitudinal direction is joined to the elastic band member on a side of the slit close to an opening end of the waist surrounding opening, or on a side of the slit close to the crotch region.

In at least a part of the front and back body regions of the back sheet, a stretchable elastic member which has a length sufficient to obtain an extended state in the wearing state is attached to a position adjacent to the absorber so as to extend along the waist surrounding opening.

A second absorber is attached to the skin contact sheet.

The skin contact sheet is coated with the second absorber, and the absorber is constituted of a mixture of a super absorbent polymer (SAP) and micro-fibrillated cellulose.

BRIEF DESCRIPTION OF DRAWINGS

FIG. 17 is a middle sectional view extending to the back body region from the front body region of a second embodiment of the diaper according to the present invention;

FIG. 18 is a middle sectional view extending to the back body region from the front body region of still another embodiment of the diaper according to the present invention;

BEST MODE FOR CARRYING OUT THE INVENTION

Figure 1:
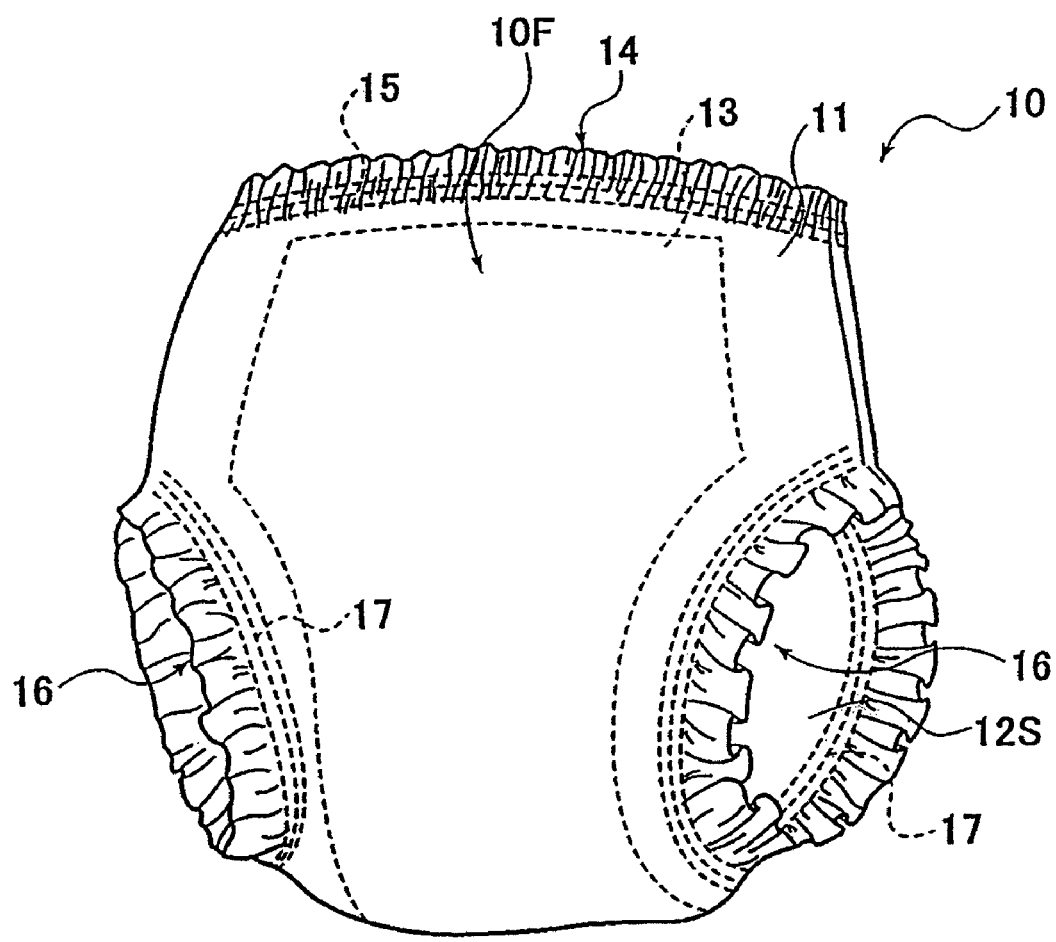
FIG. 1 is a perspective view showing an outer appearance of one embodiment of a diaper as an absorbent product according to the present invention.

As described above, the present invention relates to a mode of a skin contact sheet which is disposed on a topmost surface of an absorbent product so as to be constantly in contact with a body and which includes an opening for easier passage of excretions. Preferred modes for carrying out embodiments of the present invention will be described in detail using embodiments, and three roughly divided mode groups will be described.

The first mode group relates to a skin contact sheet which includes an opening, especially a plurality of relatively small opening portions and in which cutout portions as larger openings are combined and arranged depending on the circumstances.

The second mode group relates to a skin contact sheet which includes one opening for exclusive use in stool disposal surrounded with a relatively large stretchable band and in which cutout portions as larger openings are combined and arranged depending on the circumstances.

The third mode group relates to a skin contact sheet which includes a stretchable end flap before and/or after the sheet including a single or a plurality of openings, or cutout portions depending on the circumstances and in which a part of the end flap is joined to a waist portion so as to constantly keep a close contact state in accordance with a body movement.

Prior to the description of these three groups of embodiments, the desired basic properties, materials, and the like will be described for a skin contact sheet, back sheet, top sheet, absorber, and elastic member as basic elements constituting the present invention.

First, materials constituting the skin contact sheet as a major part of the present invention will be described.

Nonwoven cloth constituted of combined fabric, mesh sheet or film of a thermoplastic resin, and the like can be used as the constituting material of the skin contact sheet having an opening. Desired materials and shapes will be illustrated.

As the material of the skin contact sheet, it is preferred to use hydrophobic or water-repellent liquid permeable material to which liquid materials such as urine and soft stool do not easily stick, and a perforated film referred to as a dry web for use in a surface sheet of a napkin, and a filament net material particularly having stain-free property are preferred. For example, filaments of polyethylene, polypropylene, polyurethane, silicone, and Teflon (tradename: manufactured by Du Pont K.K.), and the like; or woven or knitted cloth formed of filaments of nylon or polyester and post-treated with a silicone resin or Teflon resin can be used. It is to be noted that the above-described stain-free property means a property indicating smooth passage of fluid materials such as urine and stool. In the property, a stain does not easily stick.

The skin contact sheet may have a mesh form, and Miranet (tradename: manufactured by JSP Co.) formed of foamed polyethylene by a non-crosslinked method for use as a cushion material for transport of fruits can be used.

Moreover, the skin contact sheet can be constituted of foamed resins such as a foamed styrol resin for general use as a cushion material of fruits, or stretchable elastic members such as an urethane resin and natural rubber. For example, polyethylene, polypropylene, a sheet in which a plurality of openings are formed in an extruded/molded sheet-like material of polystyrene with a foaming agent added thereto using a hot needle or suction, or an extruded/molded net of the raw material in a mesh form can also be used as the above-described foamed resins.

Miramat (tradename: manufactured by JSP Co.), Highethylene (tradename: manufactured by Hitachi Chemical Co., Ltd.), and Softron (tradename: manufactured by Sekisui Chemical Co., Ltd.) are known as the foamed resin sheet using polyethylene as the raw material. Hiethylene (tradename: manufactured by Hitachi Chemical Co., Ltd.), and P-mat (tradename: manufactured by JSP Co.) are known as the foamed resin sheet using polypropylene as the raw material. Polystyrene Paper and Miraboard (either is tradename: manufactured by JSP Co.) are known as the foamed resin sheet using polystyrene as the raw material. Among these, Miramat has soft properties, is not crosslinked, and is therefore preferred.

Moreover, the skin contact sheet may also have stretchable properties. For example, a wearer uses a net elastic structure manufactured by U.S. Conwed Co. or an elastic sheet including a fabric texture consisting of polyurethane filaments. Then, even when the wearer moves, the skin contact sheet constantly securely and comes in close contact with the skin and provides a desirable mode.

Furthermore, when dense nonwoven cloth, staple woven cloth, or knitted cloth constitutes the skin contact sheet, the urine or stool sticks among these fibers and fiber gaps are also unfavorably clogged with the urine or stool. Therefore, the sheet needs to be devised so as to partially include a large opening. Moreover, the skin contact sheet does not have to be constituted of a single sheet, and it is possible to use a skin contact sheet in which a plurality of sheets having different properties are laminated and joined in a longitudinal or width direction. For example, liquid absorbent sheets such as tissues may also be laminated. Furthermore, hydrophilic or hydrophobic nonwoven cloths may also be joined in the longitudinal or width direction. Moreover, for example, a measure in which front and back body regions are formed in different constitutions can be taken.

The absorbent product according to the present invention can also be applied to a developed type diaper in which the edges of a pair of longitudinal side flaps are overlapped with each other and fastened with a tape, or an underwear type diaper in which the ends of the pair of longitudinal side flaps are welded and bonded to each other.

As the back sheet in the present invention, it is possible to use a liquid-impervious sheet alone, or to laminate and use one to a plurality of nonwoven cloths on the sheet. As the liquid-impervious back sheet, a polyethylene sheet, particularly a polyethylene sheet in which micro holes are formed to impart air permeability, or a material having moisture permeability, such as a drawn sheet obtained by adding a filler to a thermoplastic resin, is preferably used so as to impart comfort under high humidity. In this case, the single sheet can also be used alone, but at least one nonwoven cloth may also be laminated. For example, it is possible to attach a nonwoven cloth of synthetic fiber using thermoplastic resins such as polyethylene, polypropylene, and polyester as raw materials to the surface of the back sheet for good touch. In this case, the nonwoven cloth may be either liquid-impervious or liquid-pervious.

As the top sheet, a liquid-pervious nonwoven cloth or a resin film in which a large number of pores are formed can be used. For the nonwoven cloth, a dry-forming nonwoven cloth may also be used which is formed using a synthetic fiber manufactured from polyethylene, polypropylene, and polyester or other thermoplastic resins alone as the raw material, or a mixture of a synthetic fiber with a hydrophilic fiber such as cellulose pulp or rayon fiber. To increase the liquid-pervious property, it is also effective to perform hydrophilic treatment if necessary. For the resin film in which a large number of pores are formed, a large number of pores may be formed in a film of thermoplastic resins such as polyethylene and polypropylene in a mesh form. A reason why the top sheet is used in the present invention is that an absorber component is prevented from being detached or moved. Therefore, when the absorber has a molded sheet form or a stabled sheet form, the top sheet is partially cut out in order to promote the liquid-pervious property. Alternatively, the top sheet is omitted, and the upper surface of the absorber can be allowed to function as the top sheet.

As the absorber, a super absorbent polymer (SAP) is preferably used together with a main material of fluff pulp including wood pulp or non-wood pulp in a cotton form. Additionally, absorber paper alone, or a mixture or lamination of thermally bonded fibers is used. Moreover, a laminated structure is preferred in which the whole material is enwrapped with tissue in order to prevent such SAP from jumping out. For the absorber, in addition to the above-described constitution, a skin contact sheet may directly be coated with a coat liquid in which the super absorbent polymer (SAP) and micro-fibrillated cellulose are dispersed in an aqueous solution of propylene glycol or methanol, or a nonwoven cloth of a synthetic fiber using polyethylene, polypropylene, polyester and other thermoplastic resins as the raw materials may also be coated with the coat liquid.

It is to be noted that the above-described micro-fibrillated cellulose is a very micro fiber obtained by refining the wood pulp under high share and having an average fiber length of 0.1 mm or less.

As a stretchable band member, stretchable elastic members for use in a conventional absorbent product as an object of the present invention, such as ribbon-shaped flat rubber of natural rubber, urethane thread, thread rubber, stretchable net, and stretchable film, may be are used as such. Alternatively, a composite elastic material joined to the same sheet material as the material of the back sheet or top sheet via measures such as a hot melt adhesive and heat seal in an extended state may separately be attached for use, and may be used with an arbitrary width dimension and extension magnification.

EMBODIMENTS

Embodiments of a diaper as an absorbent product according to the present invention will be described in detail with reference to FIGS. 1 to 6. However, the present invention is not limited to these embodiments, and these can further be combined, or applied also to another technique which is to be included in the scope of the present invention described in claims of this specification. This will also similarly apply to the following.

Figure 2:
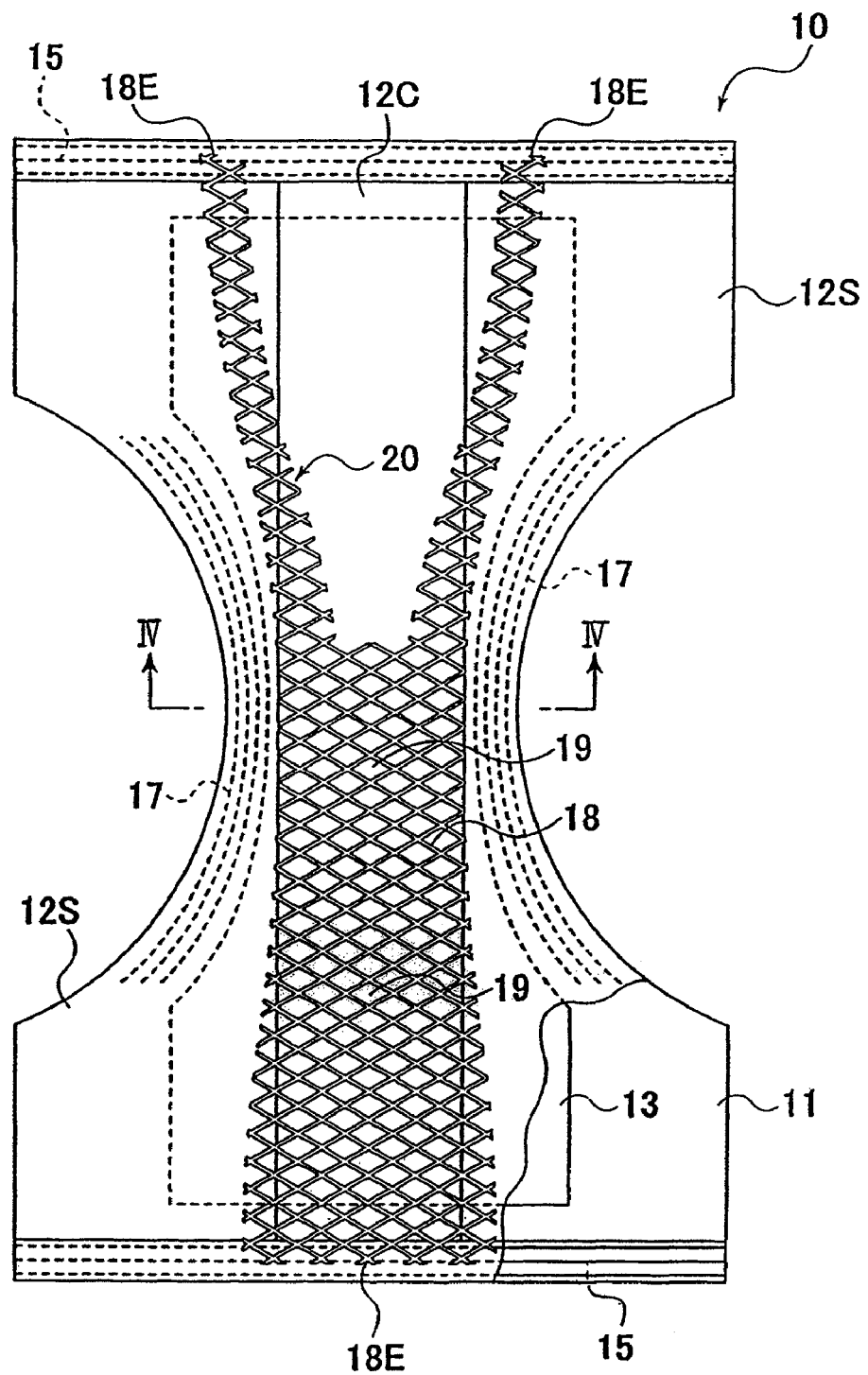
FIG. 2 is a plan view showing a developed state of the diaper shown in FIG. 1.
Figure 3:
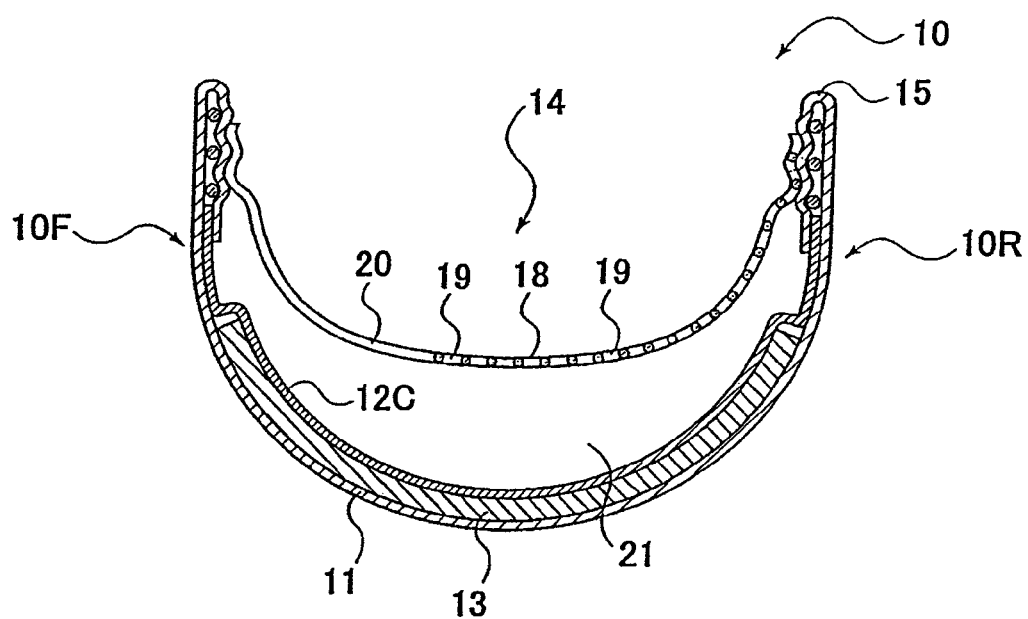
FIG. 3 is a sectional view of a middle portion extending to a back body region from a front body region of the diaper shown in FIG. 1.
Figure 4:
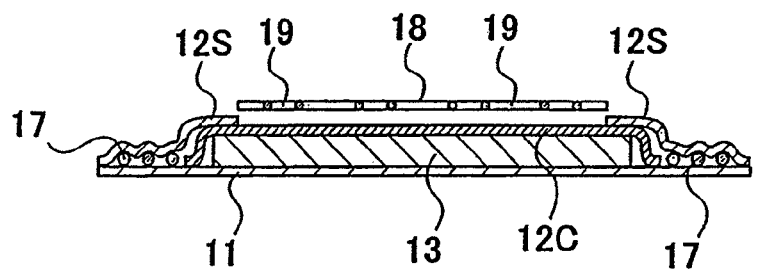
FIG. 4 is a IV-IV arrow sectional view in FIG. 2.

An appearance of the diaper according to a first group of embodiments as one mode of the absorbent product of the present invention is shown in FIG. 1, a developed configuration thereof is shown in FIG. 2, a middle sectional shape extending to a back body region from a front body region is shown in FIG. 3, and a IV-IV arrow view sectional structure of FIG. 2 is shown in FIG. 4. That is, a diaper 10 in the present embodiment has an underwear shape as a whole, and includes: a liquid-impervious back sheet 11 constituting a so-called diaper cover; a liquid-pervious center top sheet 12C to be overlapped with a width-direction middle portion of the back sheet 11; a pair of liquid-pervious left and right side top sheets 12S to be overlapped with width-direction opposite side edges of the back sheet 11 so that inner side edges of the top sheets are overlapped with width-direction opposite side edges of the center top sheet 12C having a given width; an absorber 13 which is disposed among the back sheet 11 and center top sheet 12C, and pair of left and right side top sheets 12S (hereinafter referred to collectively and roughly as the top sheets 12) and which extends to a back body region 10R from a front body region 10F of the diaper 10 and which substantially includes a sheet of a sand clock shape; a plurality of stretchable waist surrounding elastic members 15 which are held by turnup portions (waist surrounding opening 14) in an extended state along the waist surrounding opening 14 of the diaper 10; a plurality of stretchable leg surrounding elastic members 17 which are held between the back sheet 11 and top sheet 12 in an extended state along leg surrounding openings 16 of the diaper 10; and a skin contact sheet 18 which is disposed on the top sheet 12 to extend to the back body region 10R from the front body region 10F of the diaper 10 and in which longitudinal-direction opposite ends 18E are bonded to the turnup portions of the back sheet 11 on a top sheet 12 side. In the present embodiment, the top sheet 12 is divided into the center top sheet 12C and one pair of left and right side top sheets 12S, but these can naturally be constituted of a single sheet.

Moreover, a sheet base material coated with a mixture of a super absorbent polymer (SAP) and micro-fibrillated cellulose, or a pulpless sheet of the mixture of SAP and micro-fibrillated cellulose held between the sheet base materials is used as the absorber 13 in the present embodiment. When this pulpless sheet is used, the thickness of the absorber 13 can be set to be very small, and therefore wearable properties are satisfactory. This pulpless sheet is superior in water absorbing property and shape holding property, and the pulp is not used as a basic constitution. Therefore, even after the liquid is absorbed, a wet state does not last. Miscellaneous bacteria breeding is not easily caused, and therefore the sheet is also superior in hygiene aspect. As the pulpless sheet, Mega Thin® (tradename: manufactured by Japan Absorbent Technology Institute) of a nonwoven cloth coated with a mixture of SAP and micro-fibrillated cellulose, or a sheet having a mixture of SAP and micro-fibrillated cellulose held between the tissues is known.

It is to be noted that as the absorber 13, the above-described pulpless sheet and pulp may be used in combination. In this case, it is also possible to dispose the pulpless sheet over the whole lower surface of the pulp sheet, or to dispose the pulpless sheet in a portion where an absorption amount of urine is to be increased in a concentrated manner.

For the skin contact sheet 18 in the present embodiment, a large number of mesh openings 19 are formed over the whole surface of a foamed polyethylene resin molded in a net shape, the longitudinal-direction opposite ends 18E are bonded to the turnup portion of the back sheet 11 in an extended state, and the sheet can stretch along the longitudinal direction. In this case, the stool is guided into a gap 21 between the skin contact sheet 18 and top sheet 12 via a large number of openings 19 formed in the skin contact sheet 18.

An open area ratio of the skin contact sheet 18, that is, a ratio of the area of the openings 19 occupied per unit area of the skin contact sheet 18 is preferably in a range of 10 to 90%. When the open area ratio is lower than 10%, the stool does not easily pass through the skin contact sheet 18. Conversely, when the ratio exceeds 90%, the skin contact sheet 18 drops in strength, and the stool passes through the openings 19 of the skin contact sheet 18 and easily turns back.

It is to be noted that in the present embodiment a cutout portion 20 substantially having a V shape is formed in a width-direction middle portion of a portion constituting a front body region of the diaper 10. Since the cutout portion 20 is formed in this manner, the urine can be guided into the absorber 13 from the top sheet 12 without passing through the skin contact sheet 18. Therefore, a skin of a wearer can be prevented from being wetted by the urine. However, as in the present embodiment, with the skin contact sheet 18 in which a large number of openings 19 are formed, the urine is immediately absorbed by the absorber 13 from the top sheet 12 via the openings 19 of the skin contact sheet 18, and therefore the cutout portion 20 is not necessarily required.

Since the stretchable skin contact sheet 18 extends to the back body region 10R from the front body region 10F of the diaper 10, the skin contact sheet 18 includes a hanging structure inside the top sheet 12. At a wearing time, the skin contact sheet 18 is stretched in the longitudinal direction, the skin contact sheet 18 securely abuts on the wearer's skin in a close contact state, and the gap 21 is formed between the top sheet 12 and skin contact sheet 18. Therefore, even when the skin contact sheet 18 is in close contact with the wearer's skin, the high humidity state can be prevented. Additionally, even when the wearer moves in any direction, any one of the mesh openings 19 can be kept in an opened state, and the stool can securely be guided onto the top sheet 12 through the openings 19.

It is to be noted that the wearer's urine can quickly be absorbed into the absorber 13 from the top sheet 12 by the cutout portion 20 of the skin contact sheet 18 without passing through the skin contact sheet 18. Moreover, in the above-described embodiment, the underwear type diaper 10 has been described, but the present invention can also be applied in a developed-type diaper in which opposite sides of the front body region 10F of the diaper 10 are overlapped with the opposite sides of the back body region 10R and fastened with tapes.

Stretchable elastic members for conventional use in the so-called disposable diaper, such as flat rubber of natural rubber, urethane thread, and thread rubber, are used as the elastic members 15, 17 arranged in the waist surrounding opening 14 and leg surrounding openings 16, and bonded and fixed using a hot melt adhesive.

Figure 5:
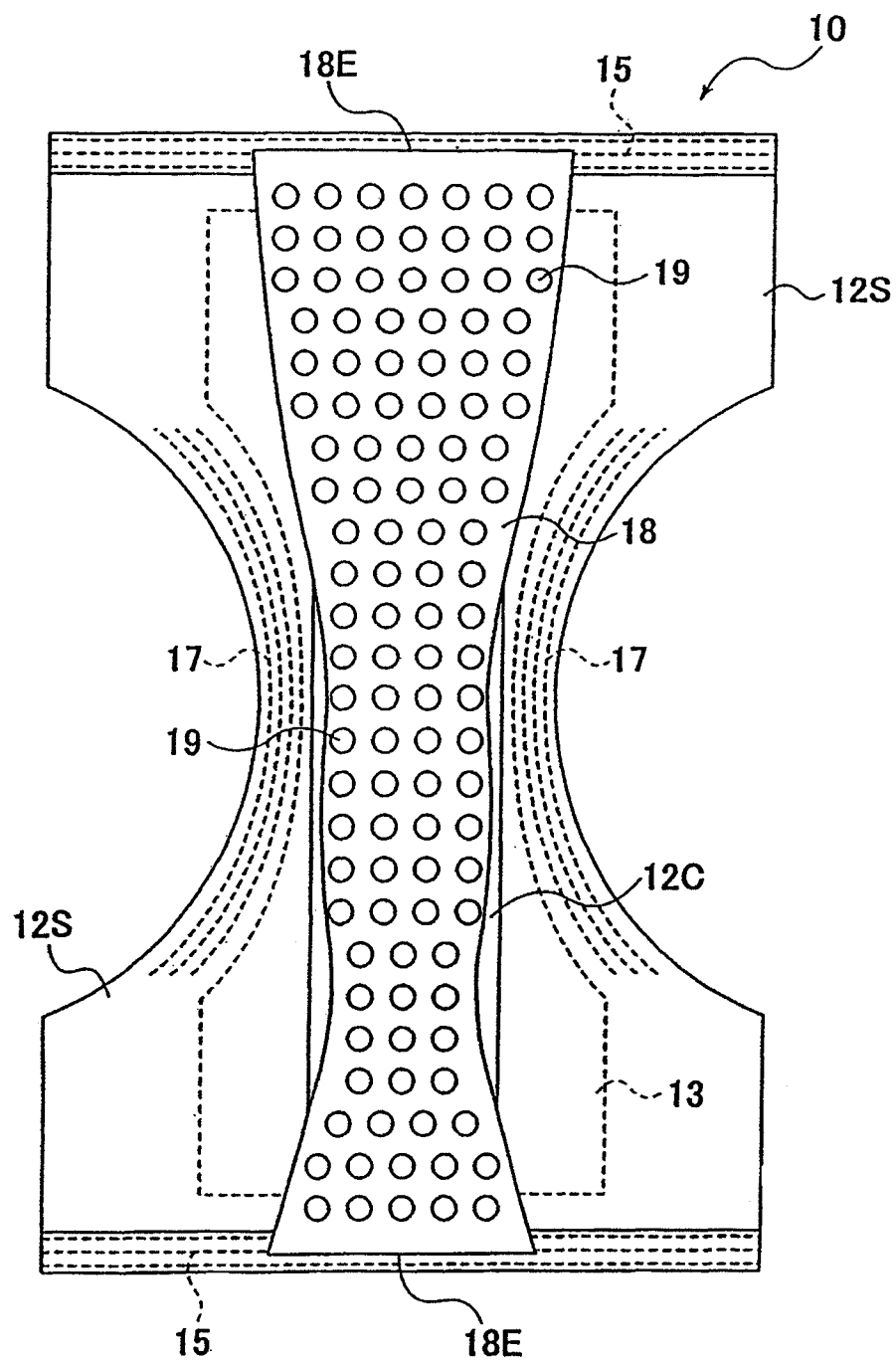
FIG. 5 is a plan view showing a developed state of another embodiment of the diaper according to the present invention.

In the above-described embodiment, the foamed resin molded in the net shape is used as the skin contact sheet 18, but a sheet in which a large number of openings are mechanically formed may also be used as the skin contact sheet 18. A developed configuration of another embodiment of the diaper according to the present invention is shown in FIG. 5, the same function members as those of the above embodiment are denoted with the same reference numerals, and redundant descriptions are omitted. That is, the skin contact sheet 18 in the present embodiment is formed of a stretchable sheet elastic member, and a large number of circular openings 19 are formed at predetermined intervals. Each of the openings 19 has a diameter of 3 mm or more, preferably 5 mm or more, and the openings 19 are arranged at such a density that the skin contact sheet 18 is not broken by these openings 19.

In addition to the circular shape as in the present embodiment, the shape of the opening 19 can appropriately be selected from rectangular, elliptical, and triangular shapes and a shape including a plurality of slits carved in the skin contact sheet 18 in an intersecting manner.

Figure 6:
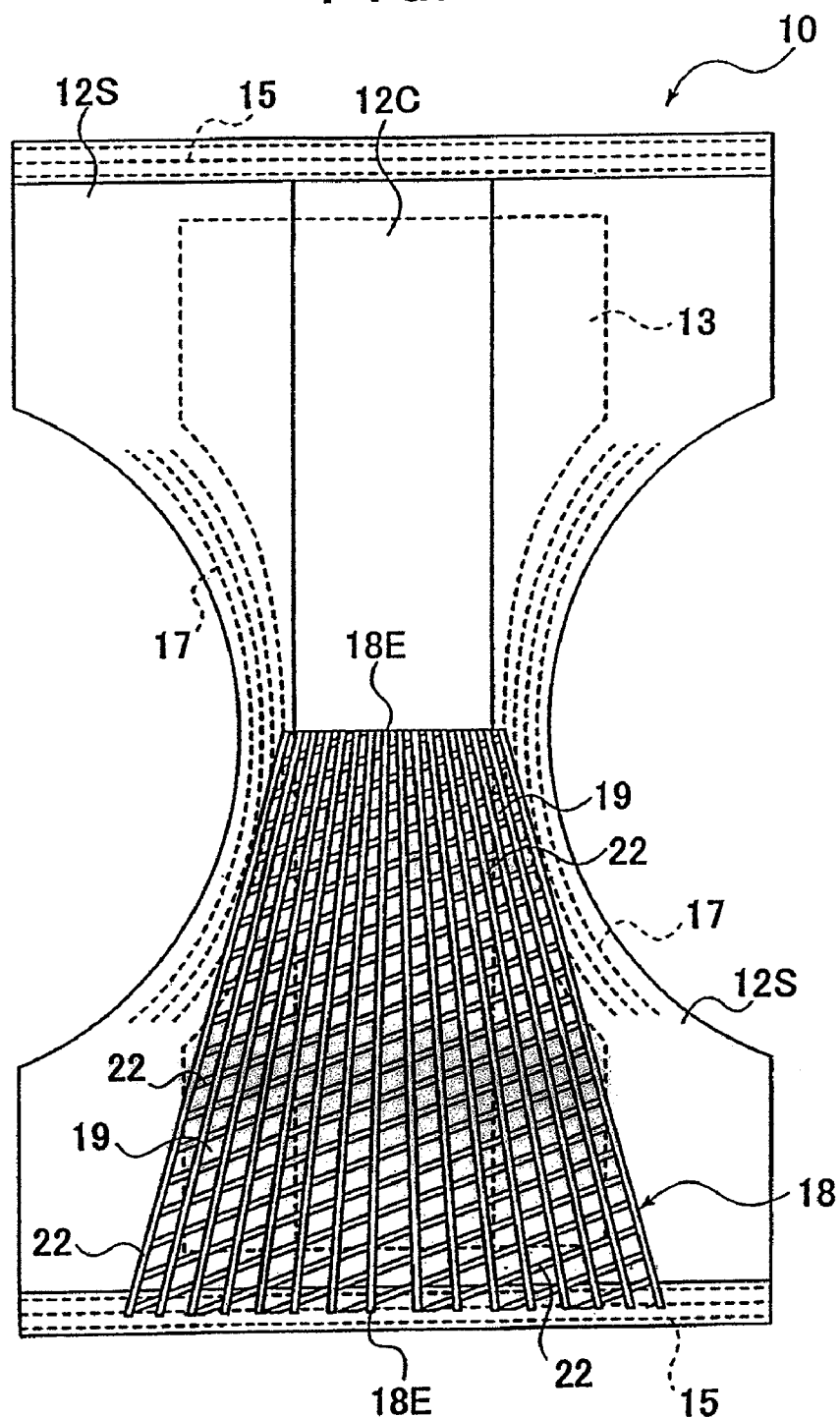
FIG. 6 is a plan view showing a developed state of another embodiment of the diaper according to the present invention.

In the above-described embodiment, the skin contact sheet 18 is formed to the back body region 10R from the front body region 10F of the diaper 10, but may be disposed to the back body region 10R from at least a crotch region. A developed configuration of a second embodiment of the diaper according to the present invention is shown in FIG. 6, the same function elements as those of the above embodiment are denoted with the same reference numerals, and the redundant description is omitted. That is, for the skin contact sheet 18 in the present embodiment, stretchable elastic ribbons 22 are arranged in longitudinal and transverse directions at predetermined intervals, these intersecting portions are integrally joined to one another, and the sheet includes a large number of openings 19 each forming a rectangle surrounded with four elastic ribbons 22. The skin contact sheet 18 is disposed to the back body region 10R from the crotch region of the diaper 10 in an extended state, and the longitudinal-direction opposite ends 18E are joined to the top sheet 12 and the turnup portion of the back sheet 11 positioned in a middle portion of a crotch region.

Also in the present embodiment, the stool is guided into the gap 21 (not shown: see FIG. 3) formed between the skin contact sheet 18 and the top sheet 12 via the openings 19 of the skin contact sheet 18, and the urine is absorbed by the absorber 13 from the top sheet 12 in the front body region 10F of the diaper 10.

According to one mode (first group) of the above-described diaper of the present invention, a plurality of openings are formed in the skin contact sheet which is disposed on the top sheet and in which at least longitudinal-direction opposite ends are joined on the top sheet. Therefore, the discharged stool is guided between the skin contact sheet and top sheet via the openings, the backside of the wearer is not made dirty, and as a result skin troubles can be avoided.

When the cutout portion is formed in the width-direction middle portion of the front body region of the skin contact sheet, the urine can be guided into the absorber from the top sheet without passing through the skin contact sheet.

When the skin contact sheet is in the form of a net shape, the stool can quickly be guided into a portion between the skin contact sheet and top sheet.

When the skin contact sheet is constituted of a foamed resin, feeling of wear can be kept to be satisfactory.

When the skin contact sheet is constituted of a stretchable elastic member, the skin contact sheet can securely be brought into close contact with the wearer.

When the absorber includes a mixture of a super absorbent polymer (SAP) and micro-fibrillated cellulose, the thickness of the diaper is reduced and the feeling of wear can be kept to be satisfactory.

Figure 7:
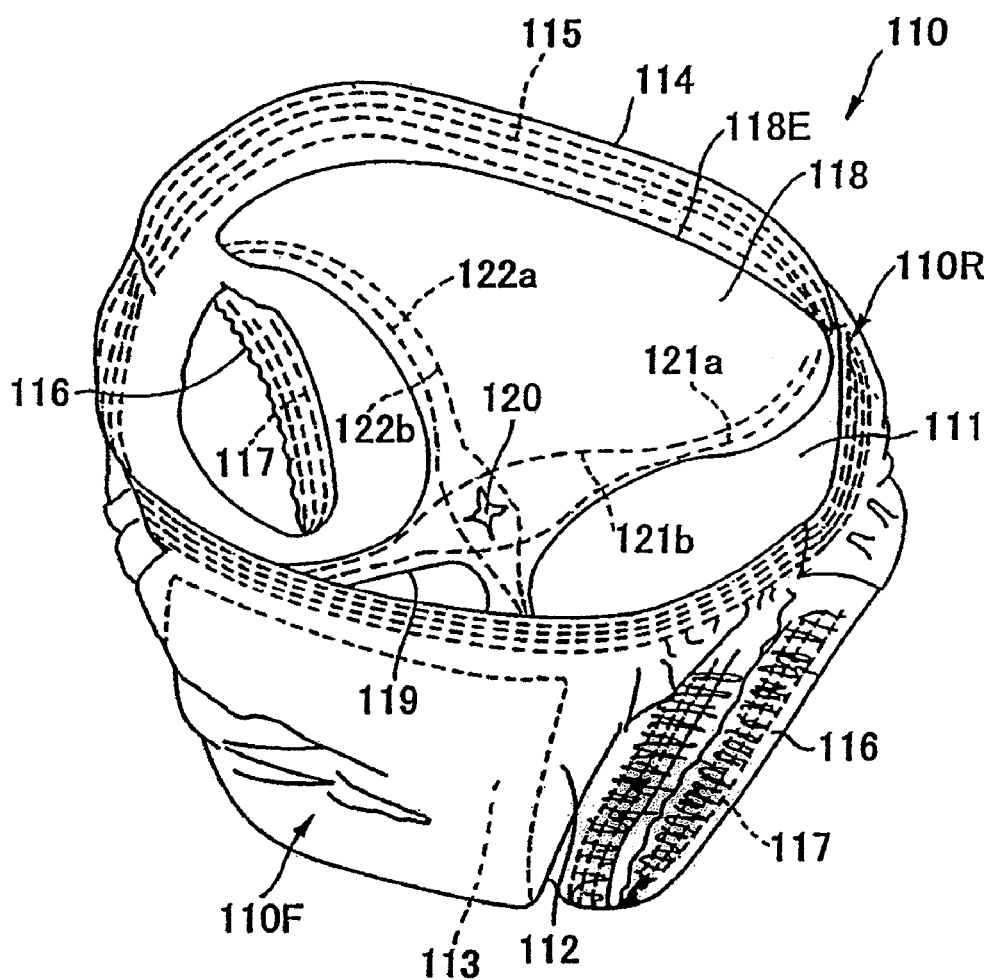
FIG. 7 is a perspective view showing an appearance of one embodiment of the diaper according to the present invention.
Figure 8:
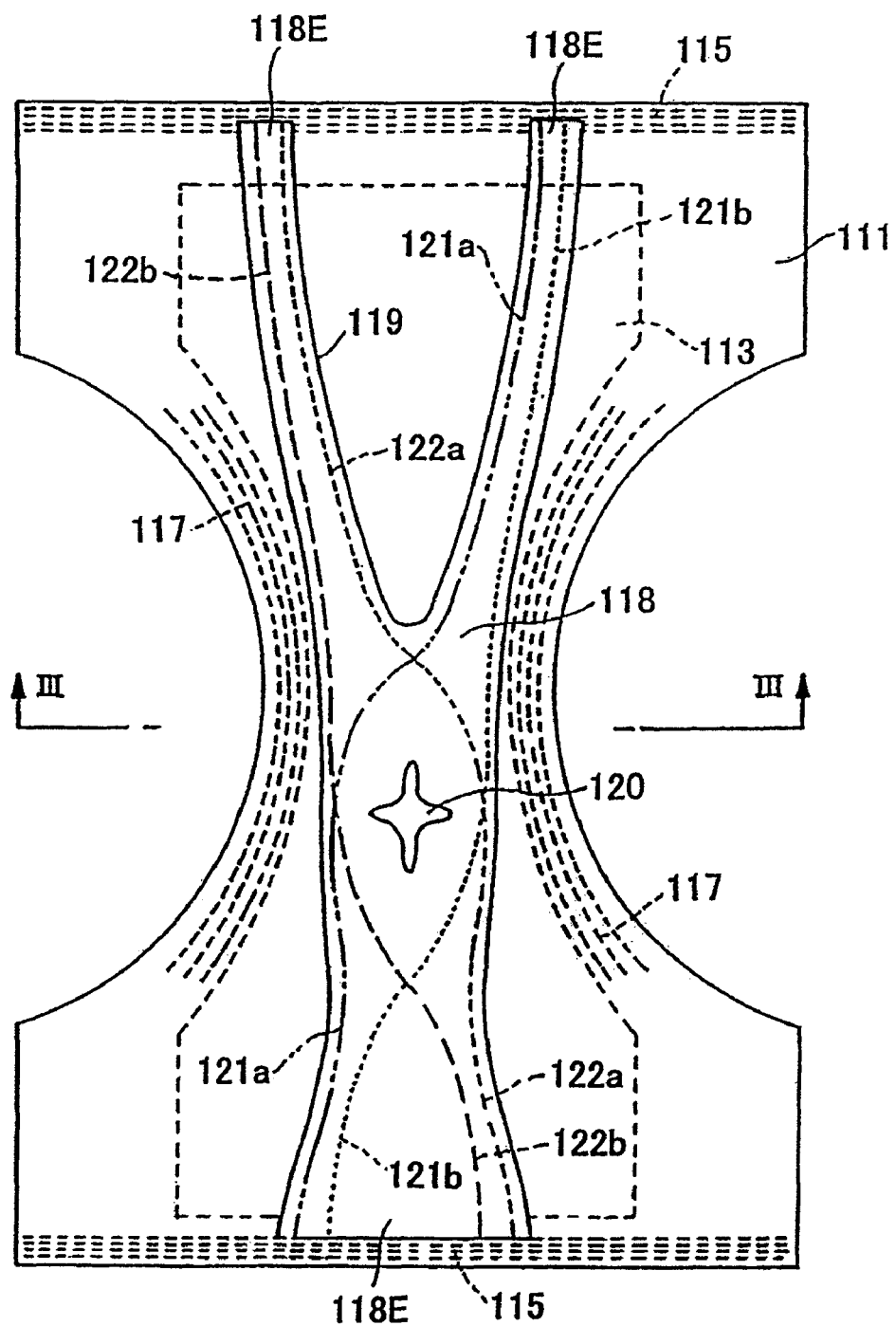
FIG. 8 is a development view of the diaper shown in FIG. 7.
Figure 9:
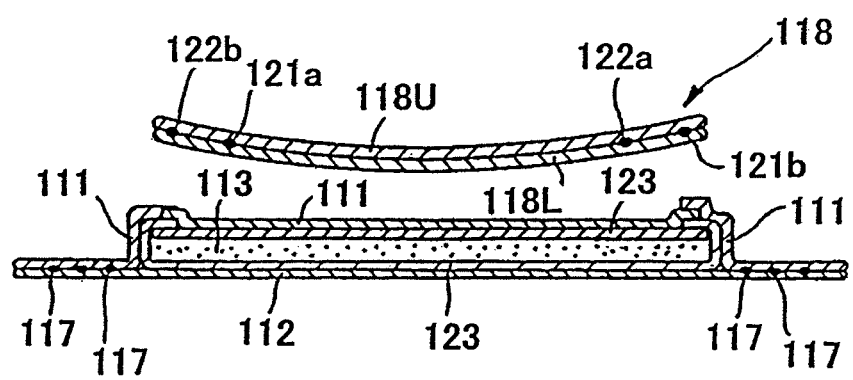
FIG. 9 is a III-III arrow sectional view in FIG. 8.
Figure 10:
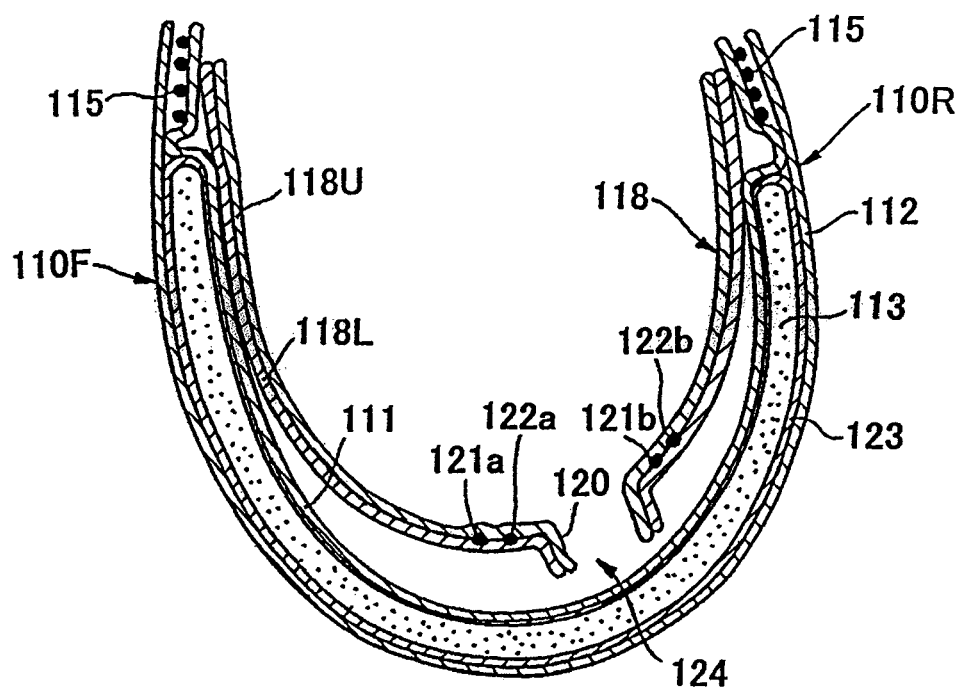
FIG. 10 is a middle sectional view extending to the back body region from the front body region of the diaper in the embodiment shown in FIG. 7.

An appearance of the diaper according to a second group of embodiments as another mode of the absorbent product of the present invention is shown in FIG. 7, a developed configuration thereof is shown in FIG. 8, a III-III arrow view sectional structure is shown in FIG. 9, and the middle sectional shape extending to the back body region from the front body region of the diaper in the embodiment is shown in FIG. 10. That is, a diaper 110 in the present embodiment includes: a liquid-pervious top sheet 111 constituting the underwear type as the whole; a liquid-impervious back sheet 112 to be overlapped with the top sheet 111; an absorber 113 which is disposed between the top sheet 111 and back sheet 112 and which extends to a back body region 110R from a front body region 110F of the diaper 110 and which substantially includes a sheet of a sand clock shape; a plurality of stretchable waist surrounding elastic members 115 which are held between the top sheet 111 and back sheet 112 in an extended state along a waist surrounding opening 114 of the diaper 110; a plurality of stretchable leg surrounding elastic members 117 which are held between the top sheet 111 and back sheet 112 in an extended state along leg surrounding openings 116 of the diaper 110; a skin contact sheet 118 which is disposed on the top sheet 111 to extend to the back body region 110R from the front body region 110F of the diaper 110 and in which longitudinal-direction opposite ends 118E are joined to the top sheet 111; a cutout portion 119 which is formed in a width-direction middle portion of the portion constituting the front body region of the diaper 110 of the skin contact sheet 118 and which is substantially in the form of a V shape or U shape; an opening 120 formed in the portion forming the crotch region of the diaper 110 in the middle portion of the skin contact sheet 118; and two sets of four stretchable elastic members 121a, 121b, 122a, 122b joined in an extended state along the longitudinal direction of the skin contact sheet 118 so as to surround the opening 120.

The skin contact sheet 118 in the present embodiment includes an upper sheet 118U and a lower sheet 118L overlapped with each other, and the above-described two sets of elastic members 121a, 121b, 122a, 122b are held between the upper sheet 118U and lower sheet 118L. One set of elastic members 121a, 121b pass through the crotch region from a width-direction one end of the front body region so as to hold the opening 120, and extend to the width-direction other end of the back body region. The other set of elastic members 122a, 122b pass through the crotch region from the other end of the width direction of the front body region so as to hold the opening 120, and extend to the width-direction one end of the back body region. That is, two sets of elastic members 121a, 121b, 122a, 122b are arranged in a crossed state with respect to the skin contact sheet 118 so as to intersect with one another via the opening 120, and the opening 120 is surrounded with these two sets of elastic members 121a, 121b, 122a, 122b.

As the top sheet 111, it is preferred to use a liquid-pervious nonwoven cloth of synthetic fiber using polyethylene, polypropylene, polyester and other thermoplastic resins as the raw materials.

As the back sheet 112 constituting the so-called diaper cover, it is possible to use the liquid-impervious sheet alone, and it is also possible to use a plurality of laminated nonwoven cloths. A liquid-impervious polyethylene sheet, preferably a polyethylene sheet in which micro holes are formed for air permeability, or a liquid-impervious sheet having moisture permeability, such as a stretch-oriented sheet obtained by adding fillers to a thermoplastic resin, is preferably used as the liquid-impervious sheet. When the moisture permeability is imparted, fear of humidity state can be eliminated, and the diaper becomes more comfortable. Furthermore, to enhance feeling of touch, a nonwoven cloth of synthetic fiber using thermoplastic resins such as polyethylene, polypropylene, and polyester as the raw materials may be attached to the surface of the back sheet 112. In this case, the nonwoven cloth may be either liquid-impervious or liquid-pervious.

For the absorber 113, a super absorbent polymer (SAP) is preferably used together with the main material of fluff pulp including wood pulp or non-wood pulp in the form of cotton. Additionally, an absorber paper alone, or a mixture or lamination of thermally bonded fibers is used. Moreover, a laminated structure is preferred in which the whole material is enwrapped with a tissue 123 in order to prevent SAP from jumping out.

For the elastic members 115, 117 arranged in the waist surrounding opening 114 and leg surrounding openings 116, stretchable elastic members for use in a conventional disposable diaper, such as a flat rubber of natural rubber, urethane thread, and thread rubber, are used, and bonded and fixed using a hot melt adhesive.

A nonwoven cloth of synthetic fibers using polyethylene, polypropylene, polyester and other thermoplastic resins as the raw materials, mesh sheet, and film are used as the skin contact sheet 118. In this case, the front body region may be formed of a liquid-pervious nonwoven cloth or film, and the crotch region and back body region may be formed of a liquid-impervious nonwoven cloth, mesh sheet, or film.

For the elastic members 121a, 121b, 122a, 122b, the stretchable elastic members for use in a conventional absorbent product, such as a ribbon-shaped flat rubber of natural rubber, urethane thread, thread rubber, stretchable net, and stretchable film, can be used as such, have arbitrary width dimensions, and are joined to the skin contact sheet 118 by the hot melt or heat seal with an arbitrary extension magnification. In the present embodiment, for each of the elastic members 121a, 121b, 122a, 122b, one member is used, but each member may be constituted of a plurality of members if necessary.

An arbitrary shape of the opening 120 can be used, and, for example, a circular or elliptical opening, or a star-shaped slit formed of two or more intersecting cuts can appropriately be selected.

As described above, since at least four elastic members 121a, 121b, 122a, 122b joined to the skin contact sheet extend to the back body region 110R from the front body region 110F of the diaper 110, the skin contact sheet 118 has a hanging structure inside the top sheet 111. At the wearing time, these elastic members 121a, 121b, 122a, 122b are stretched, the skin contact sheet 118 abuts on the wearer's skin in a close contact state, a gap 124 is formed between the top sheet 111 and skin contact sheet 118, and the stool is guided into the gap through the opening 120. Therefore, it is necessary to prevent the opening 120 of the skin contact sheet 118 from being closed by elastic forces of the elastic members 121a, 121b, 122a, 122b.

In the present embodiment, at the wearing time, the skin contact sheet 118 in a contracted state by the elastic members 121a, 121b, 122a, 122b is stretched into a developed configuration as shown in FIG. 8, and the middle portion of the crotch region surrounding the opening 120 is deformed into a rhombic shape by four linearly stretched elastic members 121a, 121b, 122a, 122b. However, the deformation acts substantially equally in the periphery of the opening 120, and the opening 120 is held in the rhombic portion without being closed. Moreover, since the elastic members 121a, 121b, 122a, 122b are arranged in a width-direction outer edge of the skin contact sheet 118, and the skin contact sheet 118 can abut on the wearer's skin to prevent its position deviation. Even if the stool is not guided onto the top sheet 111 from the opening 120 of the skin contact sheet 118 and remains between the skin contact sheet 118 and the wearer's backside, the elastic members can function as a gather for preventing leak from the width-direction outer edge of the skin contact sheet 118.

It is to be noted that the wearer's urine is quickly absorbed into the absorber 13 from the top sheet 111 by the cutout portion 119 of the skin contact sheet 118 without passing through the skin contact sheet 118. Moreover, in the above-described embodiment, the underwear-type diaper 110 has been described, but the present invention can also be applied to a developed-type diaper in which the opposite sides of the front body region 110F of the diaper 110 are overlapped with the opposite sides of the back body region 110R and fastened with tapes.

Furthermore, a joined pattern of the elastic members 121a, 121b, 122a, 122b with respect to the skin contact sheet 118 is not limited to the crossed pattern, and patterns shown in FIGS. 11 to 14 can also be used. Such another embodiment of the present invention will be described hereinafter, but the same function members as those of the above embodiment are only denoted with the same reference numerals, and the redundant description is omitted.

That is, each of the embodiments shown in FIGS. 11 to 14 shows a portion of the skin contact sheet 118 in a developed state. In the embodiment shown in FIG. 11, one set of the elastic members 121a, 121b pass through the crotch region from the width-direction one end of the front body region so as to hold the opening 120, and extend to the width-direction one end of the back body region. The other set of the elastic members 122a, 122b pass through the crotch region from the width-direction other end of the front body region so as to hold the opening 120, and extend to the width-direction other end of the back body region. Therefore, the elastic members 121b, 122b positioned outside the skin contact sheet 118 in the width direction are arranged along the width-direction opposite side edges of the skin contact sheet 118, but the elastic members 121a, 122a positioned inside the skin contact sheet 118 in the width direction are curved so as to surround the opening 120, and the opening 120 is surrounded by the pair of elastic members 121a, 122a. In this case, the elastic members 121a, 122b and the elastic members 121b, 122a can also be overlapped with one another, or intersect with one another in the side edge of the opening 120, but are preferably arranged not to be overlapped with one another as shown.

The reason is that with the elastic members 121a, 122b intersecting with the elastic members 121b, 122a, a tensile force around the opening 120 becomes nonuniform, the skin contact sheet 118 is wrinkled, and a sense of discomfort is possibly given to the wearer. Additionally, the elastic members 121b, 122b allows the width-direction side edges of the skin contact sheet 118 to be in close contact with the wearer. Therefore, when the elastic members 121a, 122a intersect, the close contact property of the skin contact sheet 118 is deteriorated.

In this embodiment, when the skin contact sheet 118 is stretched at the wearing time, the elastic members 121b, 122b positioned in the width-direction opposite side edges are extended. Therefore, the opening 120 is stretched on the width-direction opposite sides and simultaneously stretched in an extension direction of the elastic members 121a, 122a. In the same manner as in the above embodiment, the deformation of the opening 120 surrounded with the elastic members 121a, 122a substantially uniformly functions around the opening, and the opening 120 is held without being closed.

Figure 12:
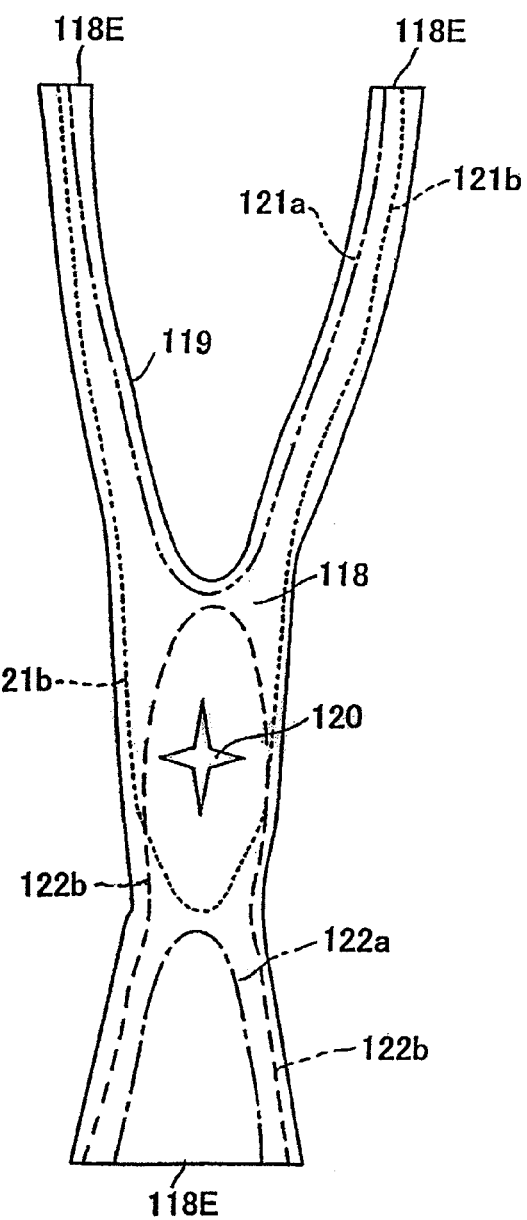
FIG. 12 is a development view of a second embodiment of the part of the skin contact sheet for use in the diaper according to the present invention.

In the embodiment shown in FIG. 12, one set of elastic members 121a, 121b pass through the crotch region from one side edge of the front body region so as to hold the opening 120, and extend to the other side edge of the front body region. The other set of elastic members 122a, 122b pass through the crotch region from one side edge of the back body region so as to hold the opening 120, and extend to the other side edge of the back body region. That is, the elastic members 121b, 122b intersect with each other over the opening 120, and the opening 120 is surrounded by the elastic members 121b, 122b. The elastic members 121a, 121b, and elastic members 121b, 122a can be arranged so as to overlap with or intersect with each other, but are preferably arranged not to overlap with each other as shown.

The reason is that with the elastic members 121a, 122b intersecting with the elastic members 121b, 122a, the tensile force around the opening becomes nonuniform, the skin contact sheet 118 is wrinkled, and the sense of discomfort is possibly given to the wearer.

Also in the present embodiment, when the skin contact sheet 118 is stretched at the wearing time, the elastic members 121b, 122b surrounding the opening 120 is held in an extended state. In the same manner as in the above embodiment, the deformation of the opening 120 surrounded with the elastic members 121b, 122b substantially uniformly functions around the opening, and the opening 120 is held without being closed.

Figure 11:
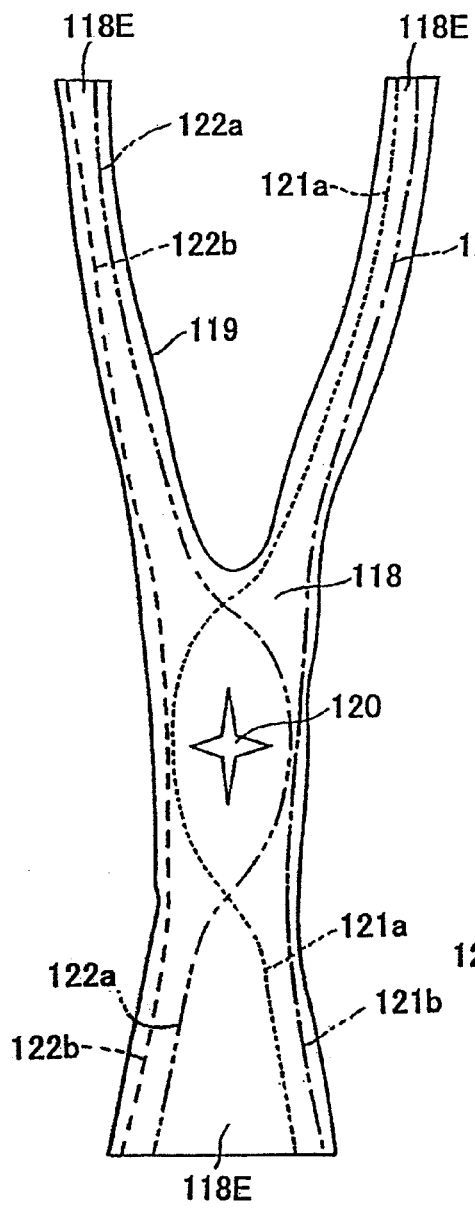
FIG. 11 is a development view of another embodiment of a part of a skin contact sheet for use in the diaper according to the present invention.
Figure 13:
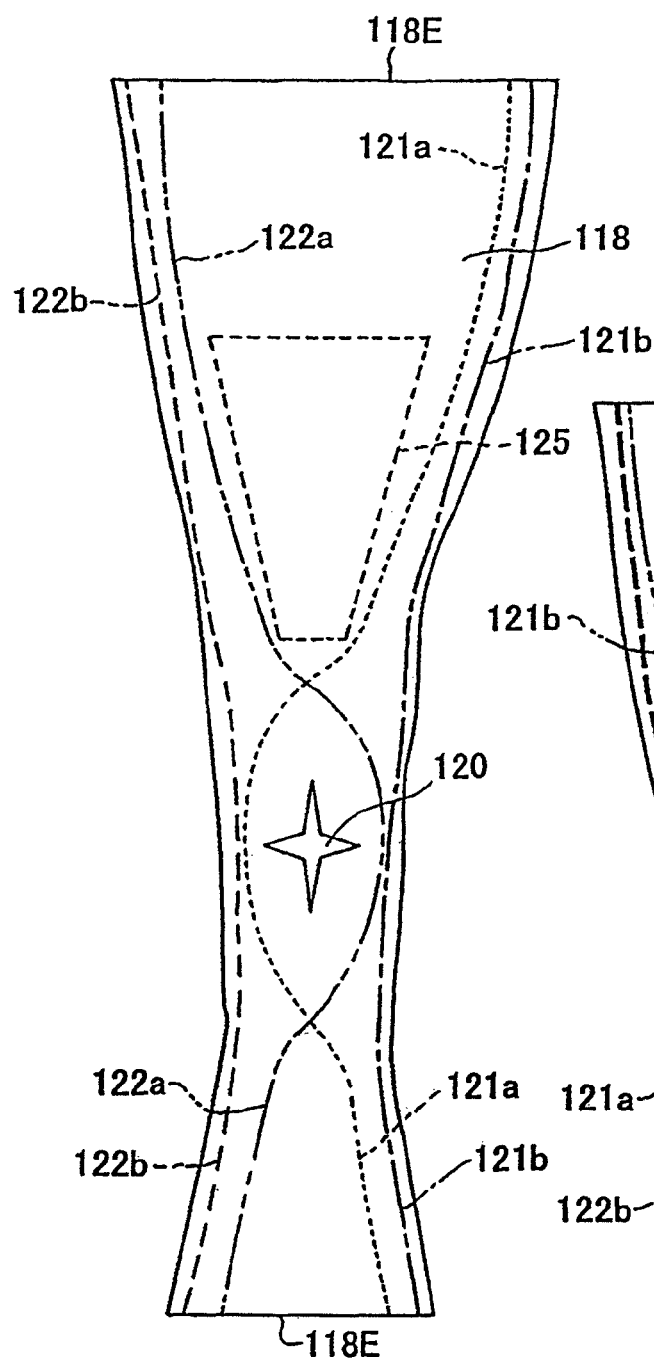
FIG. 13 is a development view of still another embodiment of the part of the skin contact sheet for use in the diaper according to the present invention.
Figure 15:
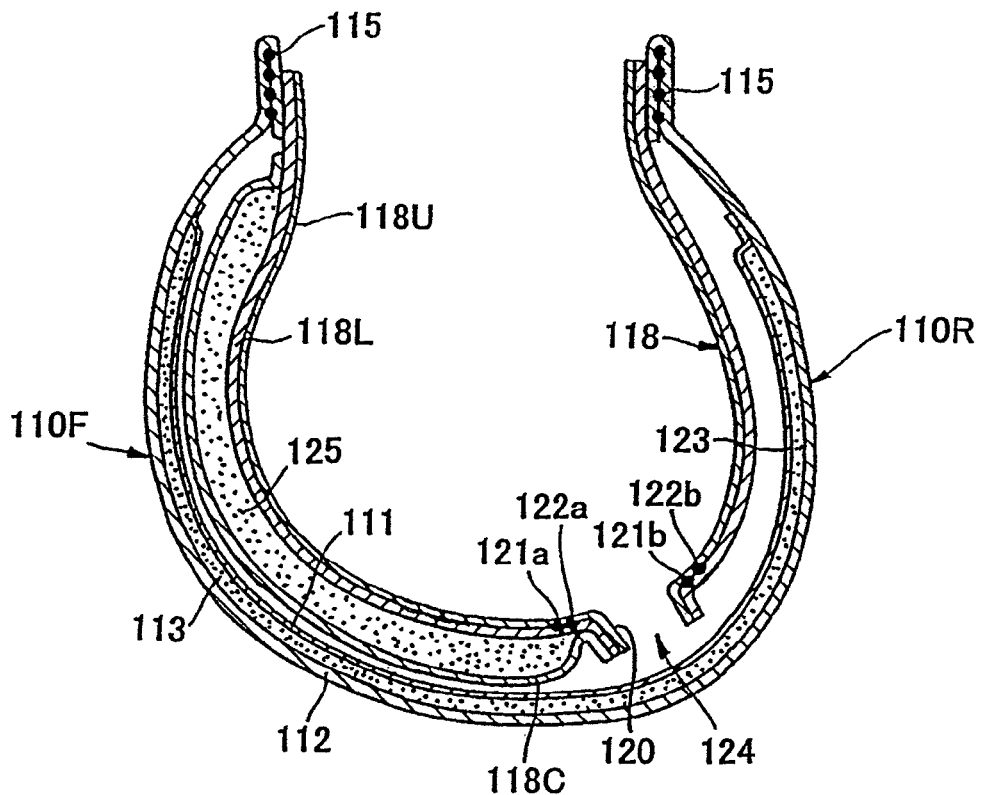
FIG. 15 is a middle sectional view extending to the back body region from the front body region of the diaper in an embodiment corresponding to FIG. 13.

In the embodiment shown in FIG. 13, the cutout portion 119 as shown in the embodiment shown in FIG. 11 is removed, a second absorber 125 forming a trapezoid is disposed instead in the front body region of the skin contact sheet 118, and a middle sectional shape extending to the back body region from the front body region is shown in FIG. 15. That is, when the second absorber 125 is disposed in the front body region of the skin contact sheet 118, the thickness of the absorber 113 can be set to be entirely small, and the skin contact sheet 118 can be kept to be in a dry state even after urination. In the present embodiment, the second absorber 125 covered with a cover sheet 118C is disposed on the back side of the lower sheet 118L, but it is also possible to dispose the second absorber 125 between the upper sheet 118U and lower sheet 118L. For the second absorber 125, the same constitution as that of the above-described absorber 113 can also be used, but it is preferred to directly coat the skin contact sheet with a coat liquid in which the super absorbent polymer (SAP) and micro-fibrillated cellulose are dispersed in a mixed solution of propylene glycol or methanol and water, or attach a web obtained by coating a nonwoven cloth consisting of synthetic fibers using polyethylene, polypropylene, polyester and other thermoplastic resins as the raw materials with the coat liquid to the skin contact sheet.

It is to be noted that the above-described micro-fibrillated cellulose is a very micro fiber obtained by refining a wood pulp under high share and has an average fiber length of 0.1 mm or less.

Figure 14:
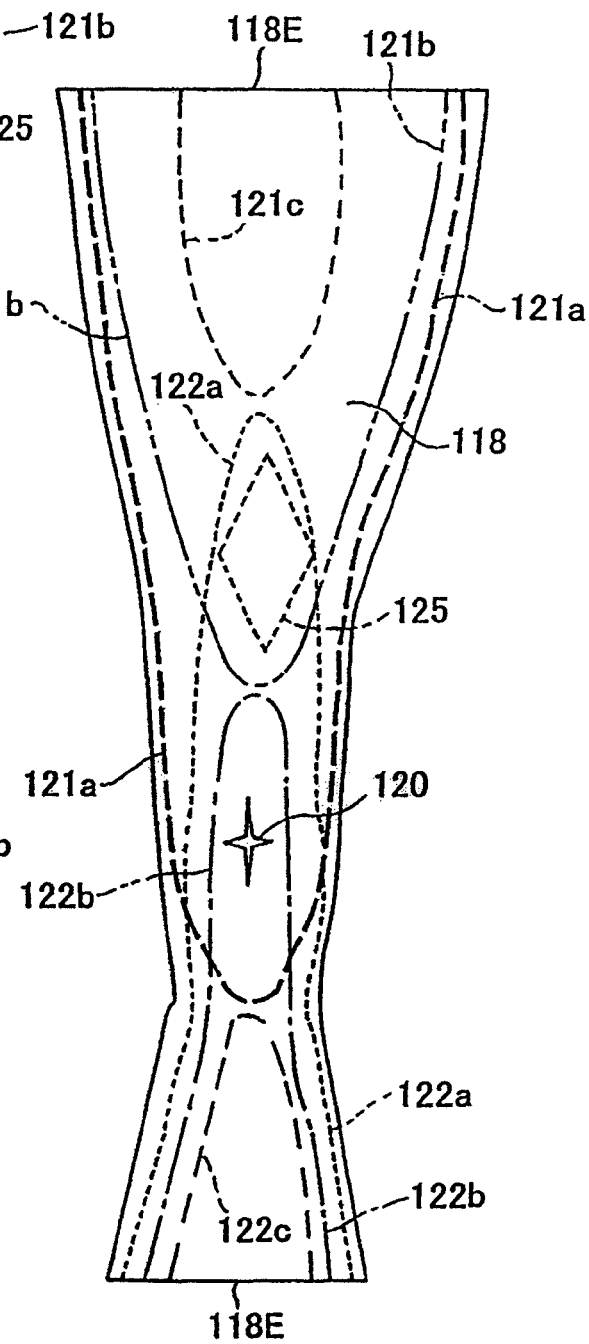
FIG. 14 is a development view of a still second embodiment of the part of the skin contact sheet for use in the diaper according to the present invention.

Also in the embodiment shown in FIG. 14, the cutout portion 119 is removed, and the second absorber 125 forming a rhombus is disposed in the front body region of the skin contact sheet 118. Furthermore, elastic members 121c, 122c are added to the embodiment shown in FIG. 12. The elastic member 121C in one set is disposed so that a bent end of the member is disposed opposite to that of the elastic member 122a in the other set. Similarly, the elastic member 122c in the other set is disposed so that the bent end of the member is disposed opposite to that of the other elastic member 121a in one set. The opening 120 is surrounded by the elastic members 121a, 122b, and the second absorber 125 is surrounded by the elastic members 121b, 122a.

The elastic members 121b, 122a are arranged in this manner, thereby a region where the second absorber 125 surrounded with the elastic members 121b, 122a is disposed forms a concave depression by contraction forces of these elastic members 121b, 122a, and the depression functions as a urine reservoir until the urine is absorbed by the second absorber 125.

Figure 16:
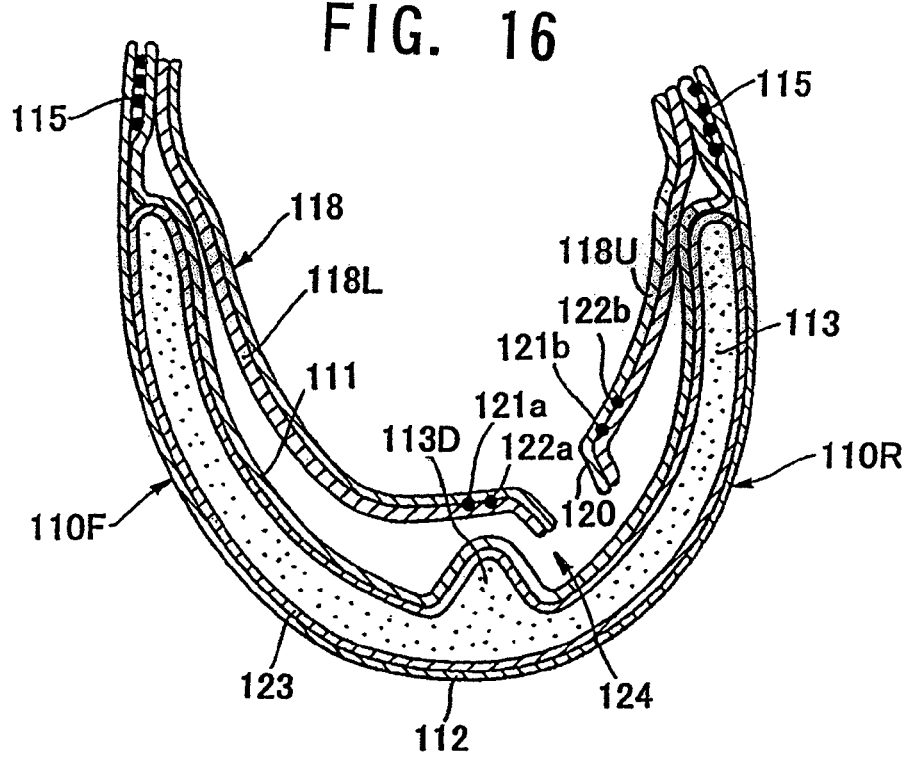
FIG. 16 is a middle sectional view extending to the back body region from the front body region of another embodiment of the diaper according to the present invention.

In order to prevent the stool from being mixed with the urine, the shape of the absorber 113 in the crotch region can be devised as shown in FIGS. 16 to 18. Still further embodiments of the present invention will be described hereinafter, but the same function members as those of the above embodiment are only denoted with the same reference numerals, and redundant descriptions are omitted.

That is, each of embodiments shown in FIGS. 16 to 18 shows the middle portion of the diaper 110 in a broken structure extending to the back body region 110R from the front body region 110F. In the embodiment shown in FIG. 16, a weir portion 113D positioned in the front body region from the opening 120 in the crotch region just under the opening 120 is formed to extend in the width direction, while the thickness of the absorber 113 is increased. Arrangements are made such that the stool guided onto the top sheet 111 from the opening 120 is prevented from easily moving to the front body region and being mixed with the urine. Conversely, the urine is prevented from easily moving to the crotch region from the front body region and being mixed with the stool.

Moreover, in the embodiment shown in FIG. 17, a waveform portion 120S which can avoid the movement of stool is formed on the surface of the absorber 113 extending to the back body region from the crotch region disposed opposite to the opening 120. On the other hand, a weir 126 for inhibiting the stool guided to the waveform portion 120S from the opening 120 from moving to the front body region is formed by the top sheet 111 along the width direction of the crotch region, and the upper end of the weir 126 is disposed to abut on the skin contact sheet 118.

In the embodiment shown in FIG. 18, the thickness of the absorber 113 extending to the back body region from the crotch region disposed opposite to the opening 120 is reduced to form a pocket portion 127, and arrangements are made such that the stool guided to the pocket portion 127 from the opening does not easily move on the top sheet 111.

According to another mode (second group) of the above-described diaper of the present invention, since the stretchable elastic member is joined to the skin contact sheet in an extended state so as to surround the opening disposed in a portion of the crotch region of the skin contact sheet, the skin contact sheet can be in close contact with the wearer. Additionally, the opening is held in an opened state by a stretching force of the elastic member, the discharged stool is guided between the skin contact sheet and top sheet via the opening, the wearer's backside is not made dirty, and, as a result, the skin trouble can be inhibited from being generated.

Moreover, two sets of two elastic members are arranged in a crossed state in the skin contact sheet so as to intersect with each other via the opening. Alternatively, at least two elastic members are passed through the crotch region from one side edge of the front body region of the diaper so as to hold the opening and extended to the other side edge of the front body region, and at least two elastic members are passed through the crotch region from one side edge of the back body region of the diaper so as to hold the opening and extended to the other side edge of the back body region. In this case, the contraction force substantially uniformly functions in the periphery of the opening. Therefore, when these elastic members are extended, the opening can securely be opened without being closed.

When the cutout portion is formed in the width-direction middle portion of the skin contact sheet forming the front body region of the diaper, the urine can quickly be absorbed by the absorber disposed between the top sheet and back sheet. In this case, when the skin contact sheet is set to be liquid-impervious, the wearer's backside can be kept in a dry state.

When the second absorber is disposed in a portion of the skin contact sheet forming the front body region of the diaper, the urine can quickly be absorbed by the absorber and can be prevented from being mixed with the stool.

Figure 19:
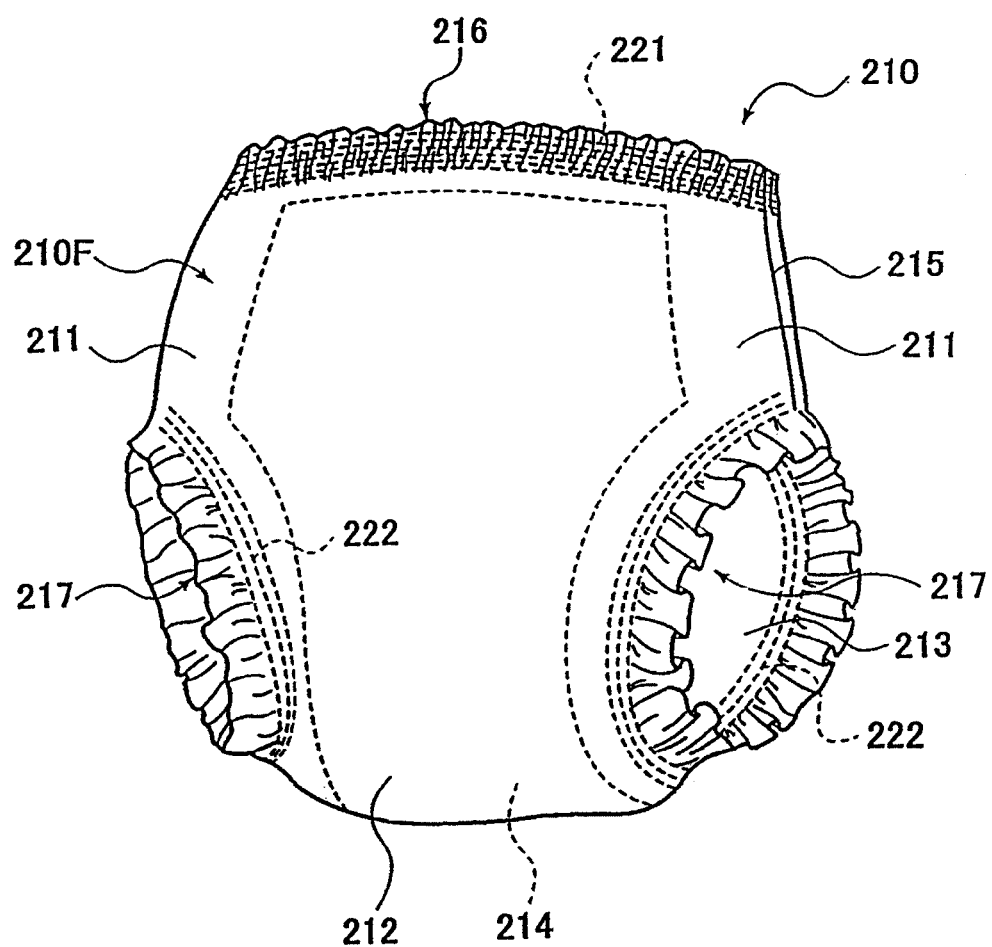
FIG. 19 is a perspective view showing the appearance of one embodiment of the diaper according to the present invention.
Figure 20:
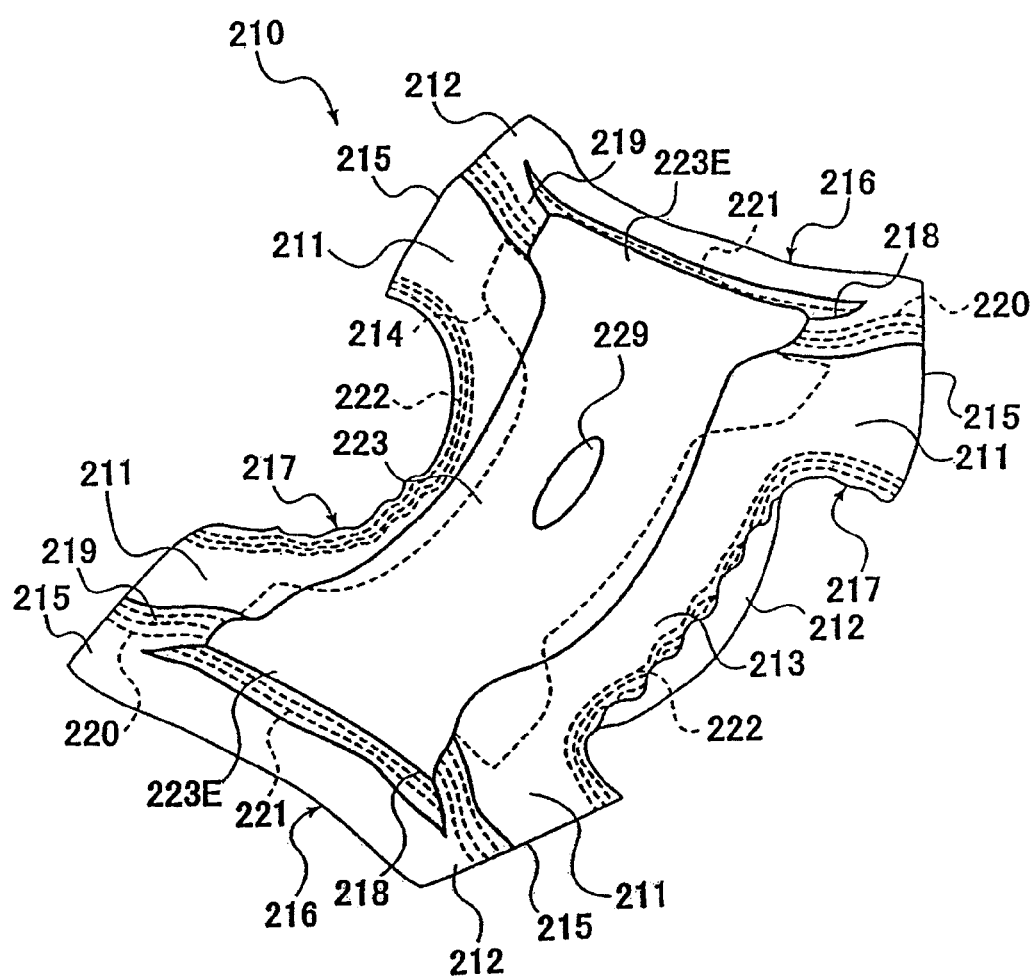
FIG. 20 is a perspective view seen from the inside in the developed state of the diaper of the embodiment shown in FIG. 19.
Figure 21:
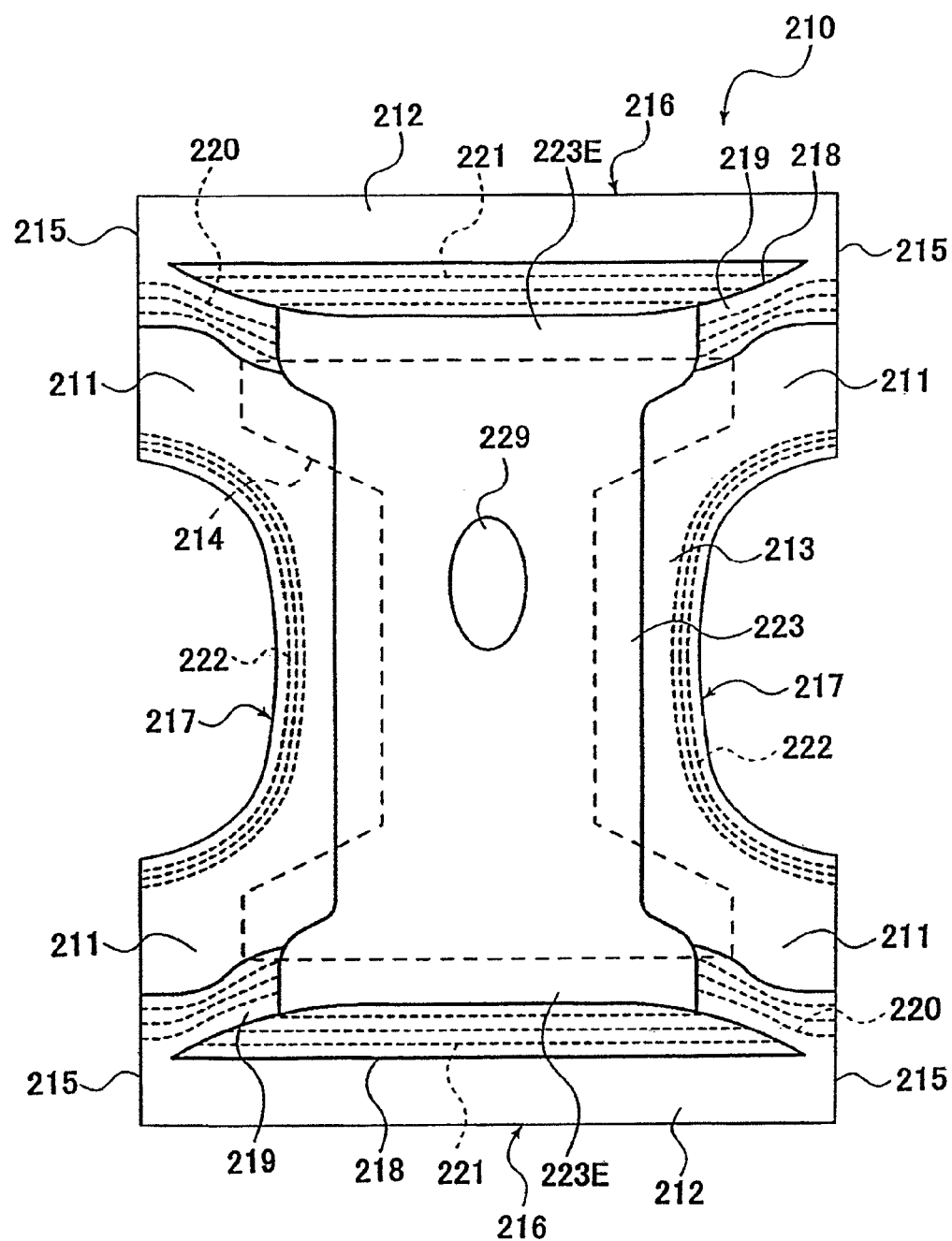
FIG. 21 is a front view on a skin contact sheet side in an extended state on a back sheet side of the diaper shown in FIG. 20.
Figure 22:
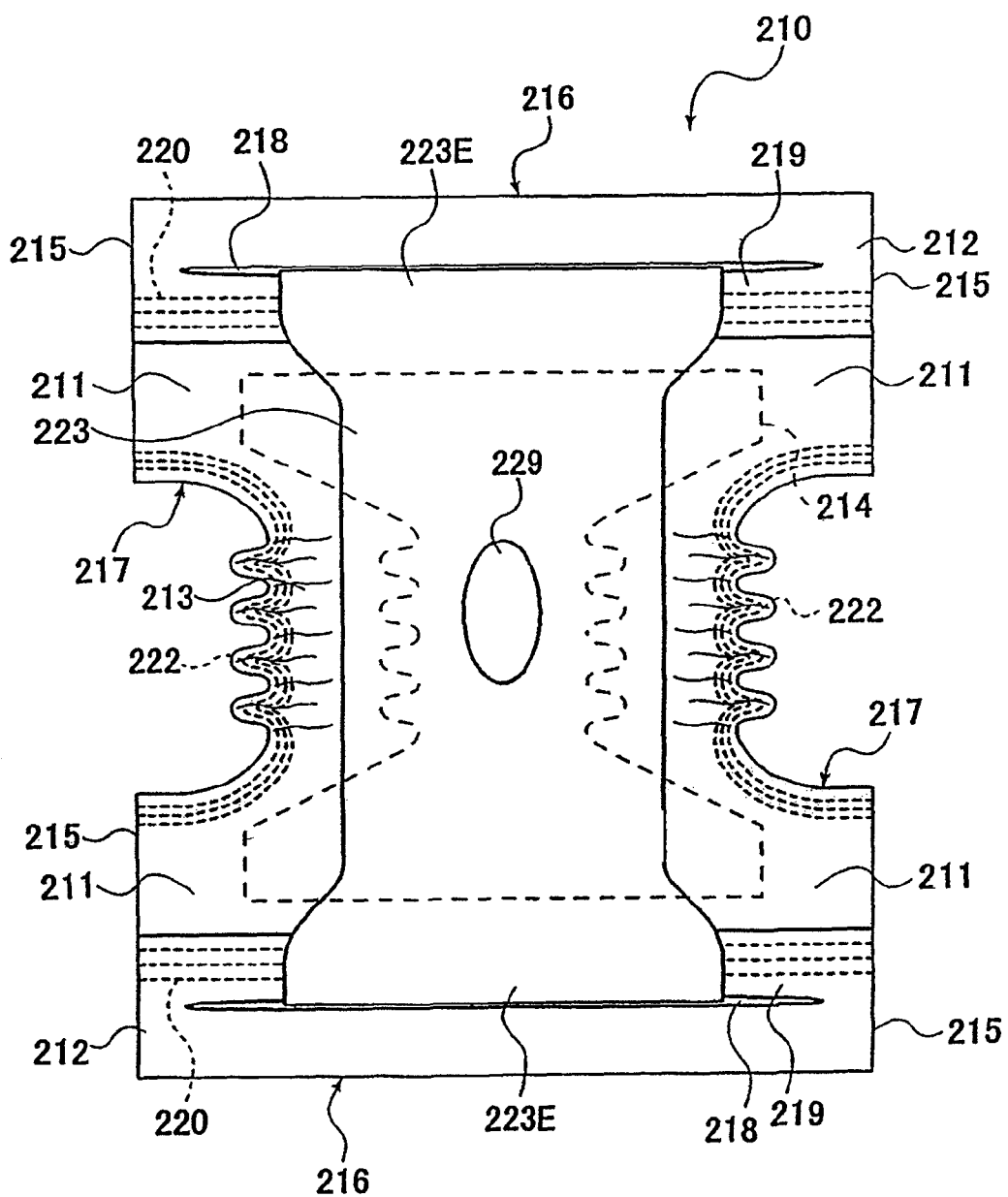
FIG. 22 is a front view on the skin contact sheet side in a non-extended state on the back sheet side of the diaper shown in FIG. 20.
Figure 23:
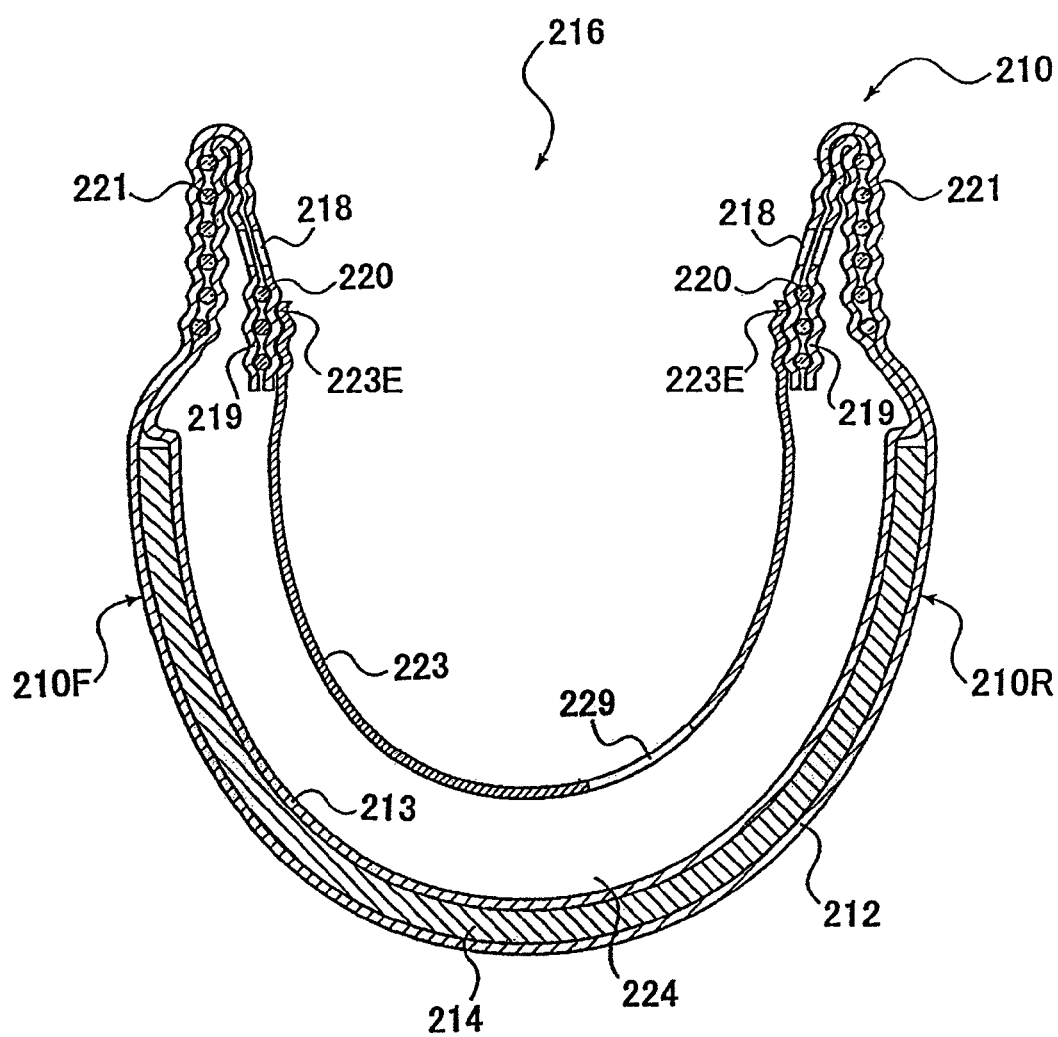
FIG. 23 is a middle sectional view extending to the back body region from the front body region of the diaper shown in FIG. 19.

An appearance of a diaper according to a third group of embodiments as another mode of the absorbent product of the present invention is shown in FIG. 19, a developed configuration thereof is shown in FIG. 20, front shapes on the skin contact sheet side in an extended or non-extended state on the back sheet side are shown in FIGS. 21 and 22, and a middle sectional shape extending to the back body region from the front body region of the diaper is shown in FIG. 23. That is, a diaper 210 in the present embodiment includes: a liquid-impervious back sheet 212 including a pair of longitudinal side flap portions 211 with which a wearer's waist is covered; a liquid-pervious top sheet 213 overlapped with the back sheet 212; and an absorber 214 which is disposed between the back sheet 212 and top sheet 213 and which extends to a back body region 210R from a front body region 210F of the diaper 210 and which substantially includes a sheet of a sand clock shape. The side edges of the pair of longitudinal side flap portions 211 are mutually fused/welded to form a joined portion 215 so that the whole forms the underwear pant shape, and thereby a waist surrounding opening 216 and a pair of right and left leg surrounding openings 217 are simultaneously formed.

In the diaper 210 in the present embodiment, end parts of a back sheet 212 and top sheet 213 constituting the waist surrounding opening 216 are turned back toward the inside (top sheet 213 side), and a pair of front and back slits 218 extending along the waist surrounding opening 216 are formed in the turnup portion, so that a pair of front and back end flaps 219 are formed and opposite ends of the flaps are fastened with the joined portion 215. In these end flaps 219 and waist surrounding opening 216, a plurality of stretchable elastic members 220 for the end flaps and waist surrounding elastic members 221 held between the top sheet 213 and back sheet 212 are disposed in an extended state along the waist surrounding opening 216. Similarly, a plurality of stretchable leg surrounding elastic members 222 held between the top sheet 213 and back sheet 212 are disposed along the leg surrounding openings 217 in an extended state.

A skin contact sheet 223 is disposed on the top sheet 213, and extends to a back body region 210R from a front body region 210F of the diaper 210, and longitudinal-direction opposite ends 223E of the sheet are joined to the pair of front and back end flaps 219. The length of the skin contact sheet 223 is set to be shorter than an interval of the pair of front and back slits 218 in an extended state. Therefore, when the back sheet 212 and 213 are in an extended state, as shown in FIG. 21, the end flaps 219 are stretched and the slits 218 are largely opened. Conversely, when the slits 218 are closed, as shown in FIG. 22, the back sheet 212 and top sheet 213 are loosened. The length of the skin contact sheet 223 is set to be shorter than the interval of the pair of front and back slits 218 in an extended state in this manner, and thereby a gap 224 can be formed between top sheet 213 and skin contact sheet 223, which comes in close contact with the skin at the wearing time of the diaper 210.

An elliptic opening 229 for guiding the stool onto the top sheet 213 from the gap 224 formed between the skin contact sheet 223 and top sheet 213 is formed in the crotch region of the skin contact sheet 223. When the skin contact sheet 223 is formed to be liquid-impervious in a region to the back body region from the crotch region, even a mixture of stool and urine is partitioned from the wearer's backside by the skin contact sheet 223, and the wearer's backside can be kept to be clean.

That is, the urine is passed through the skin contact sheet 223 and absorbed by the absorber 214 held between the top sheet 213 and back sheet 212. Moreover, the stool is guided into the gap 224 between the skin contact sheet 223 and top sheet 213 from the opening 229 formed in the crotch region of the skin contact sheet 223, and held on the top sheet 213. This can prevent the urine from being mixed with stool and reduce the occurrence of diaper rash.

Figure 24:
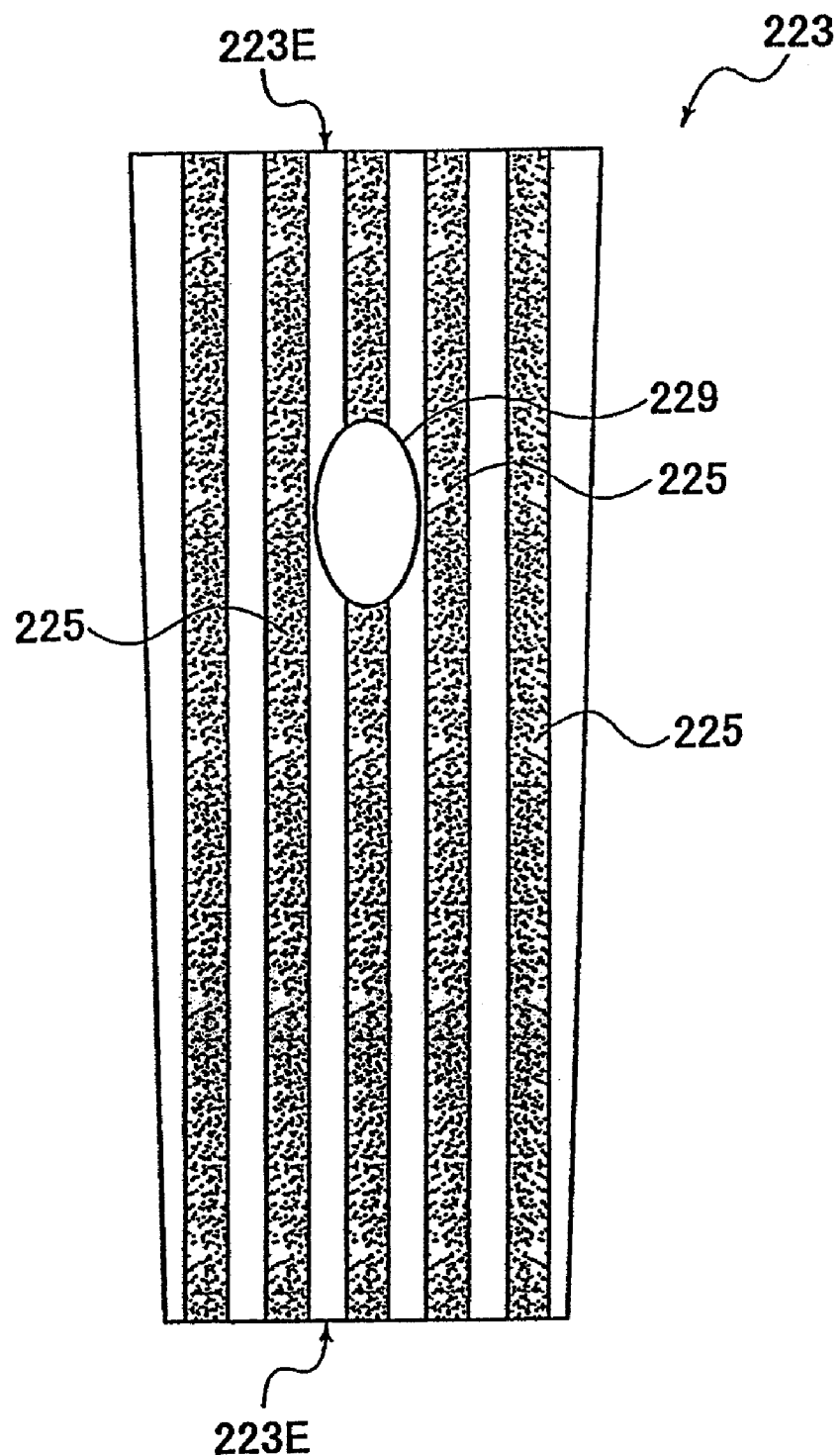
FIG. 24 is a front view showing one example of the skin contact sheet for use in the present invention.

Only the skin contact sheet 223 is extracted and shown in FIG. 24. In the skin contact sheet 223, second absorbers 225 extending along the longitudinal direction of the sheet can be formed in stripes at given intervals, and this can provide a satisfactory dry feeling of touch. The second absorbers 225 include a mixture of SAP and micro-fibrillated cellulose, and the skin contact sheet 223 is coated with the absorber, so that the thickness of the absorber can be reduced and a sense of discomfort at the wearing time can be eased.

In the above-described embodiment, the end flaps 219 are formed over the whole region of the waist surrounding opening 216, but may substantially have the same widths as those of the longitudinal-direction opposite ends 223E of the skin contact sheet 223, and the elastic members can also be disposed in regions other than the vicinity of the waist surrounding opening 216 in the front and back body regions.

Figure 25:
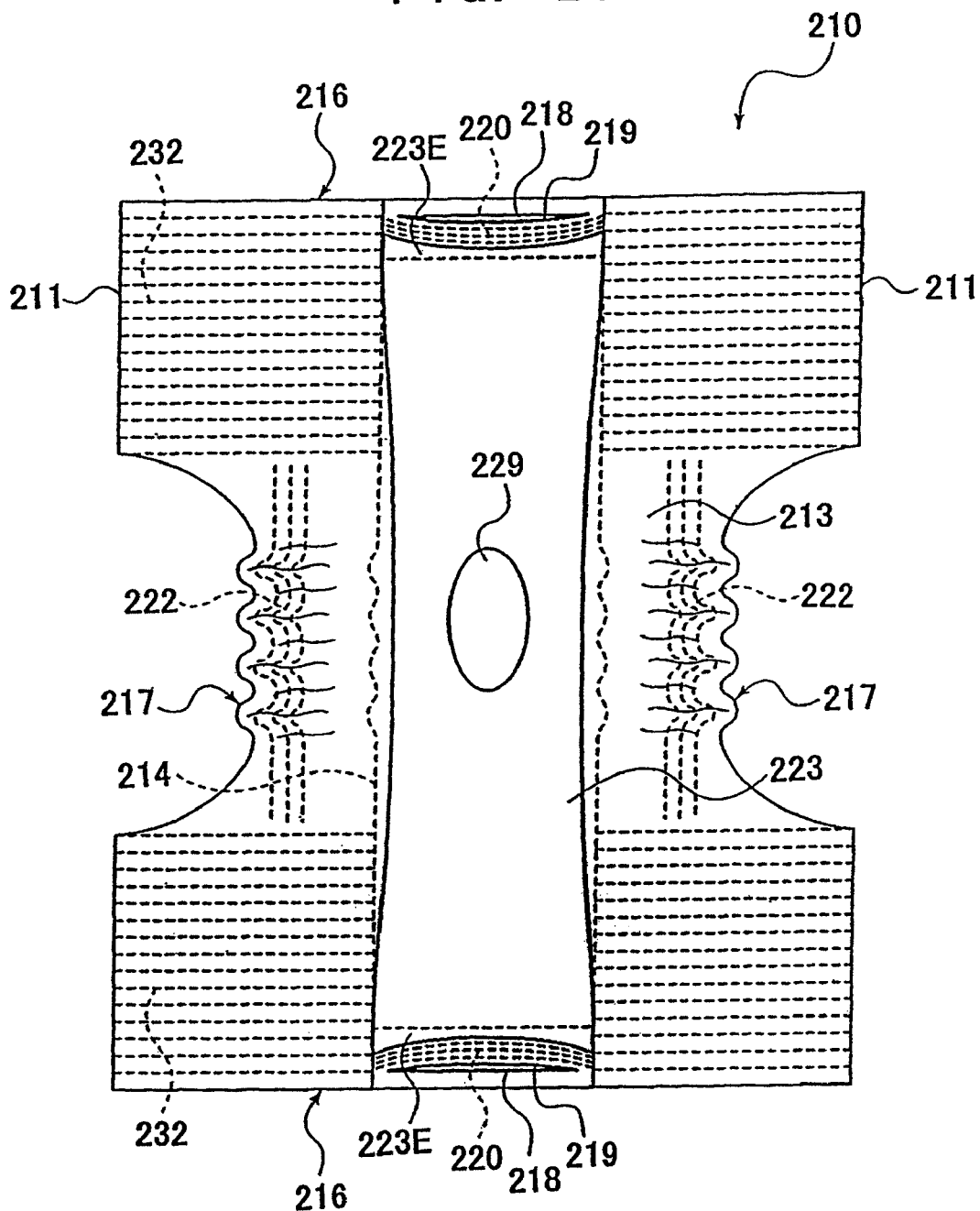
FIG. 25 is a front view on the skin contact sheet side in a non-extended state on the back sheet side in the development of another embodiment of the diaper according to the present invention.

In another embodiment of this diaper according to the present invention, a front configuration on the skin contact sheet 223 side in a developed state is shown in FIG. 25 in which the back sheet side is not extended, but the same function members as those of the above embodiment are only denoted with the same reference numerals, and redundant descriptions are omitted. That is, in the present embodiment, in a region including the side flap portions 211 between the waist surrounding opening 216 and leg surrounding openings 217 in the front and back body regions, a plurality of elastic members 232 disposed adjacent to the absorber 214 are disposed along the waist surrounding opening 216 in an extended state. Moreover, the longitudinal-direction opposite ends of the leg surrounding elastic members 222 are disposed in the vicinity of elastic member 232 of the front body region and elastic member 232 in the back body region so as to cross at right angles to these elastic members 232.

The end flaps 219 are disposed only in the width-direction middle portion of the diaper 210, and the slits 218 are formed along the waist surrounding opening 216. Moreover, a region on the waist surrounding opening 216 side from the slits 218 is joined integrally to the top sheet 213, and the plurality of elastic members for end flaps 220 are disposed in an extended state on the crotch region in a free state. The longitudinal-direction opposite ends 223E of the skin contact sheet 223 are integrally joined to the portions of the end flaps 219 on the crotch region side from the slits 218. Even in the present embodiment, the length of the skin contact sheet 223 is set to be shorter than an interval of the pair of front and back slits 218 in an extended state of the diaper 210. Thereby, the skin contact sheet 223 can be brought in close contact with the wearer's skin at the wearing time of the diaper 210.

In the above-described embodiment, at least the front body region of the skin contact sheet 223 is formed to be liquid-pervious, and thereby the urine is passed through the skin contact sheet 223 and absorbed by the absorber 214 from the top sheet 213. Moreover, when the cutout portion is formed in the width-direction middle portion of the front body region of the skin contact sheet 223, it is also possible to absorb the urine directly by the absorber 214 from the top sheet 213 without being passed through the skin contact sheet 223.

Figure 26:
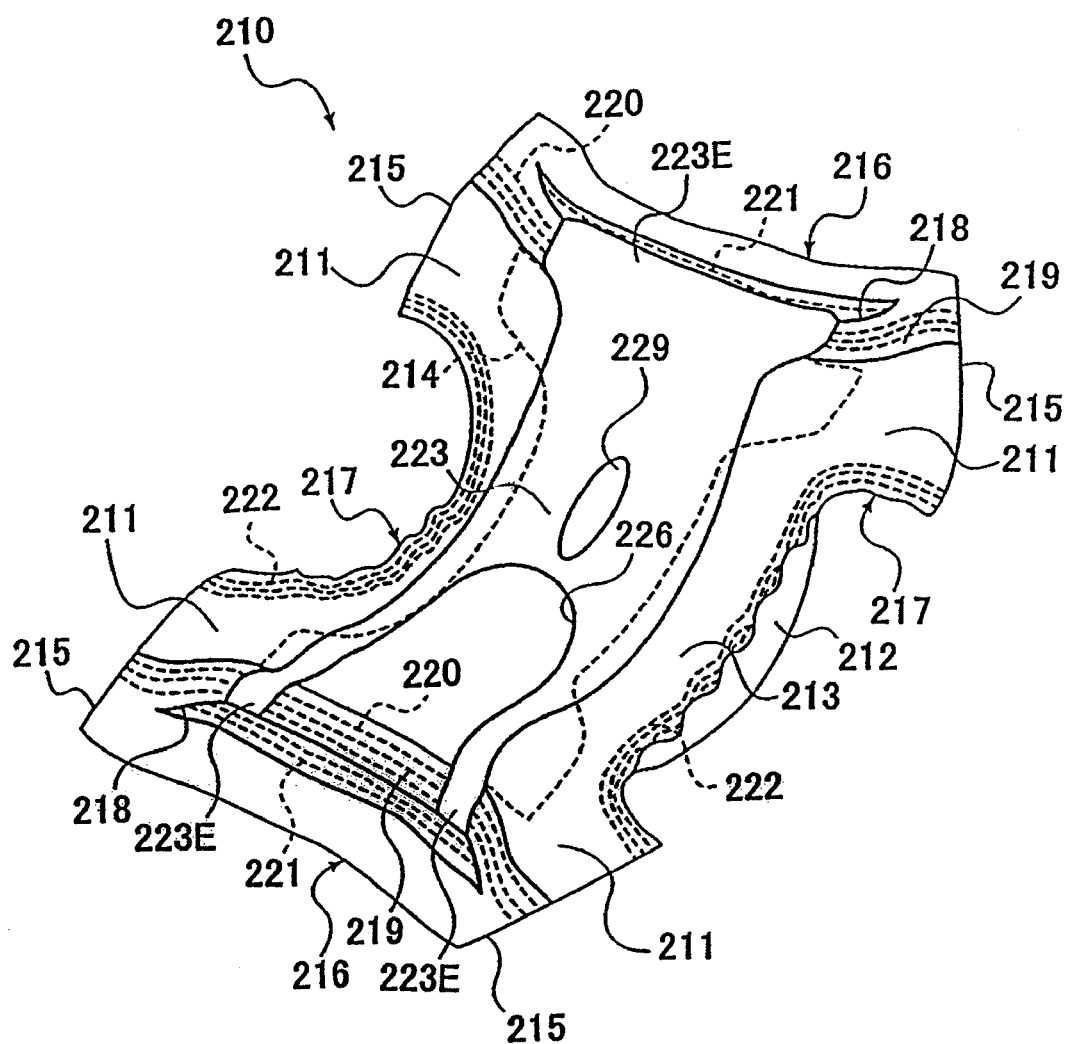
FIG. 26 is a perspective view seen from the inside in a developed state of a second embodiment of the diaper according to the present invention.

An appearance of another embodiment of this diaper according to the present invention is shown in FIG. 26 in a developed state, the same function members as those of the above embodiment are only denoted with the same reference numerals, and redundant descriptions are omitted. That is, in the present embodiment, a cutout portion 226 is formed in the width-direction middle portion of the front body region of the skin contact sheet 223 in the present embodiment, and thereby the urine is absorbed into the absorber 214 directly from the top sheet 213 not via the skin contact sheet 223. Therefore, it is also possible to form the whole skin contact sheet 223 to be liquid-impervious, and this can more securely prevent the urine from being mixed with stool.

In the above-described embodiment, the longitudinal-direction opposite ends 223E of the skin contact sheet 223 are joined to the stretchable end flaps 219. However, the slits passed to the outside from the inside of the diaper 210 are formed along the waist surrounding opening 216, and the longitudinal-direction opposite ends 223E of the skin contact sheet 223 may also be joined right in the vicinity of the waist surrounding opening side from the slit.

Figure 27:
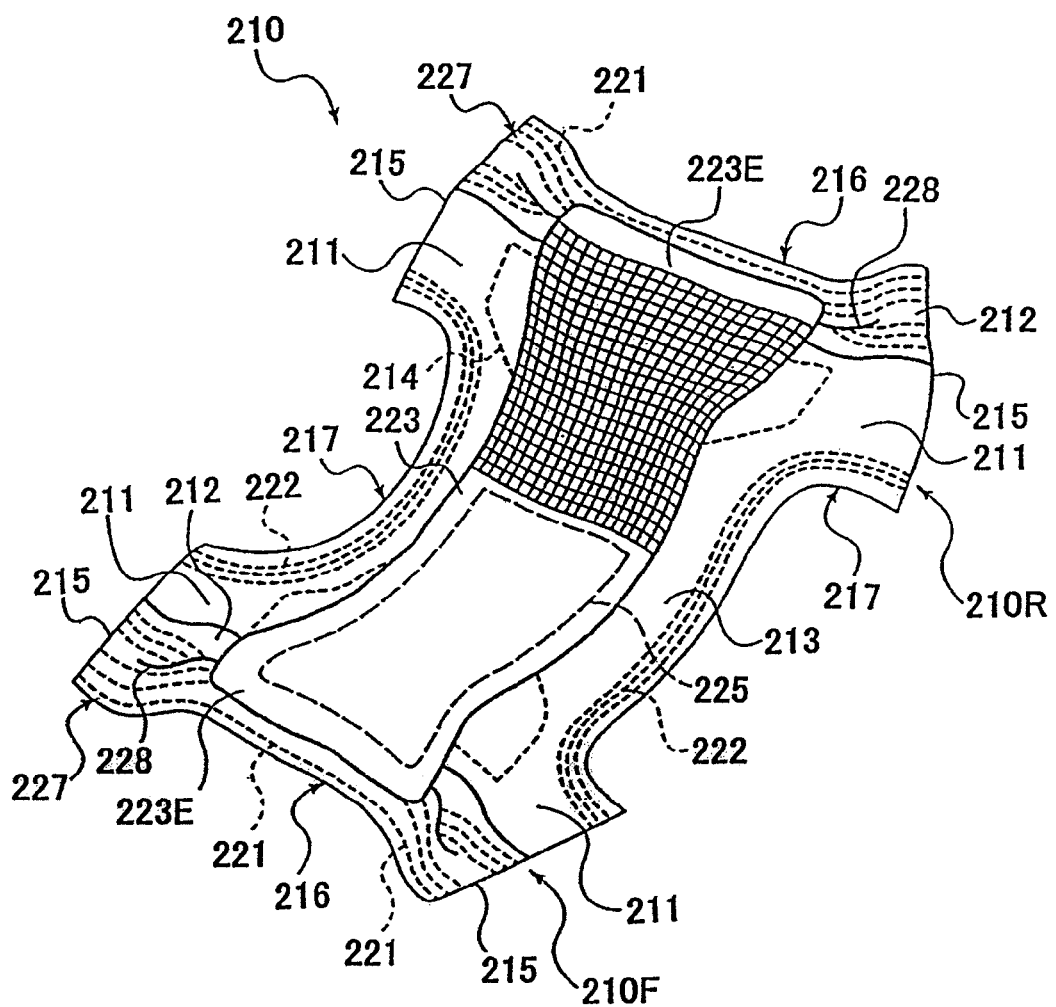
FIG. 27 is a perspective view seen from the inside in a developed state of another embodiment of the diaper according to the present invention.

An appearance of another embodiment of this diaper according to the present invention is shown in FIG. 27 in a developed state, the same function members as those of the above embodiment are only denoted with the same reference numerals, and redundant descriptions are omitted. That is, each of the longitudinal-direction opposite ends of the back sheet 212 in the present embodiment is turned back on the top sheet 213 side to form a turnup portion 227 joined integrally to the top sheet 213, and a pair of front and back slits 228 extending along the waist surrounding opening 216 are formed in the turnup portion 227. The slits 228 in the present embodiment are passed to the outside from the inside of the diaper 210. Therefore, the waist surrounding opening 216 has a tape-shaped portion in the front and back body regions of the diaper 210, and in the present embodiment this portion is joined to the longitudinal-direction opposite ends 223E of the skin contact sheet 223. The waist surrounding elastic members 221 are disposed over the whole regions of the turnup portions 227 via the slits 228. Even in the present embodiment, a distance between the front and back turnup portions 227 joined to the longitudinal-direction opposite ends 223E of the skin contact sheet 223 is set to be longer than the length of the skin contact sheet 223.

It is to be noted that the second absorbers 225 are disposed in the front body region of the skin contact sheet 223 in the present embodiment, and further the back body region is formed in a net shape to constitute the openings of the present invention.

Therefore, at the wearing time of the diaper 210, a tape-shaped portion of the waist surrounding opening 216 is stretched by the skin contact sheet 223 and extended to form a gap among the skin contact sheet 223, back sheet 212, and top sheet 213 in the same manner as in the above embodiment, and the stool is passed through the back body region of the skin contact sheet 223 having a net shape and held onto the top sheet 213.

Figure 28:
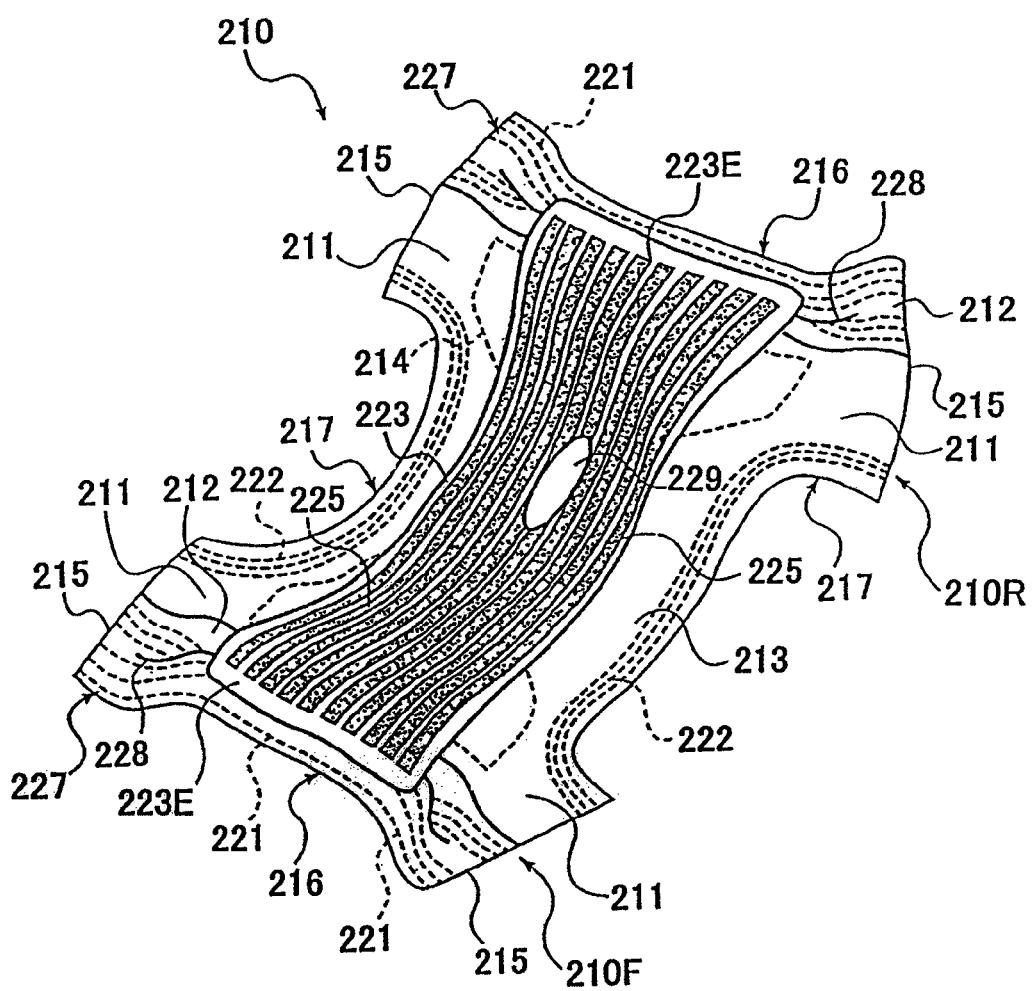
FIG. 28 is a perspective view seen from the inside in a developed state of still another embodiment of the diaper according to the present invention.

Instead of the above-described skin contact sheet 223, it is also possible to dispose the skin contact sheet 223 shown in FIG. 24 as shown in the embodiment of FIG. 28. In this case, the urine is held by the second absorbers 225 of the skin contact sheet 223, and the stool is passed through the opening 229 and held on the top sheet 213, so that the urine and stool can be prevented from being easily mixed.

Figure 29:
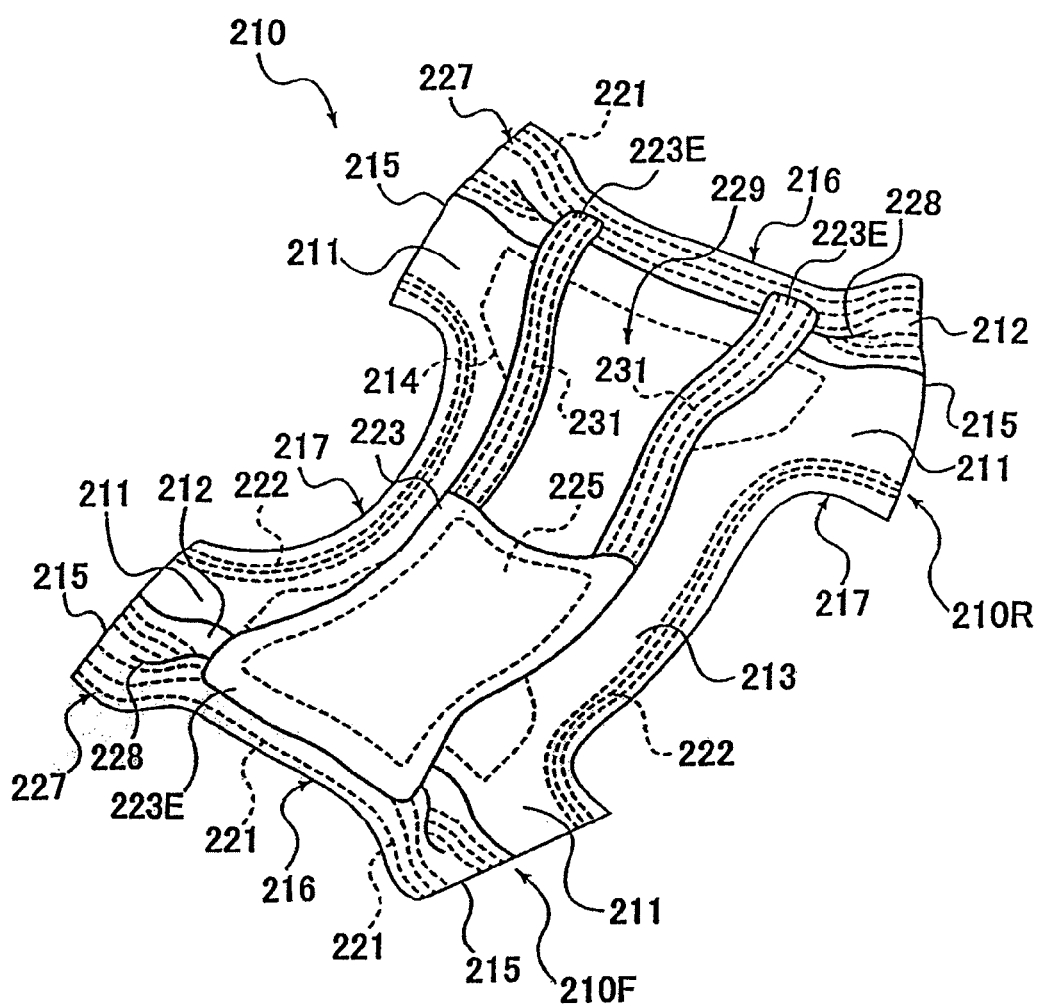
FIG. 29 is a perspective view seen from the inside in a developed state of a still second embodiment of the diaper according to the present invention.

Moreover, as shown in FIG. 29, the width-direction middle portion of the region to the back body region from the crotch region of the skin contact sheet 223 can be cut out to form the opening. In the present embodiment, stretchable elastic members 231 are disposed in an extended state in the back body region of the tape-shaped skin contact sheet 223, and thereby arrangements are made such that the skin contact sheet 223 is securely in close contact with the wearer's skin at the wearing time.

In this manner, the constitution of the skin contact sheet 223 can arbitrarily be changed if necessary. Moreover, in FIGS. 28-29, the same function parts as those of the above embodiment are denoted with the same reference numerals.

Figure 30:
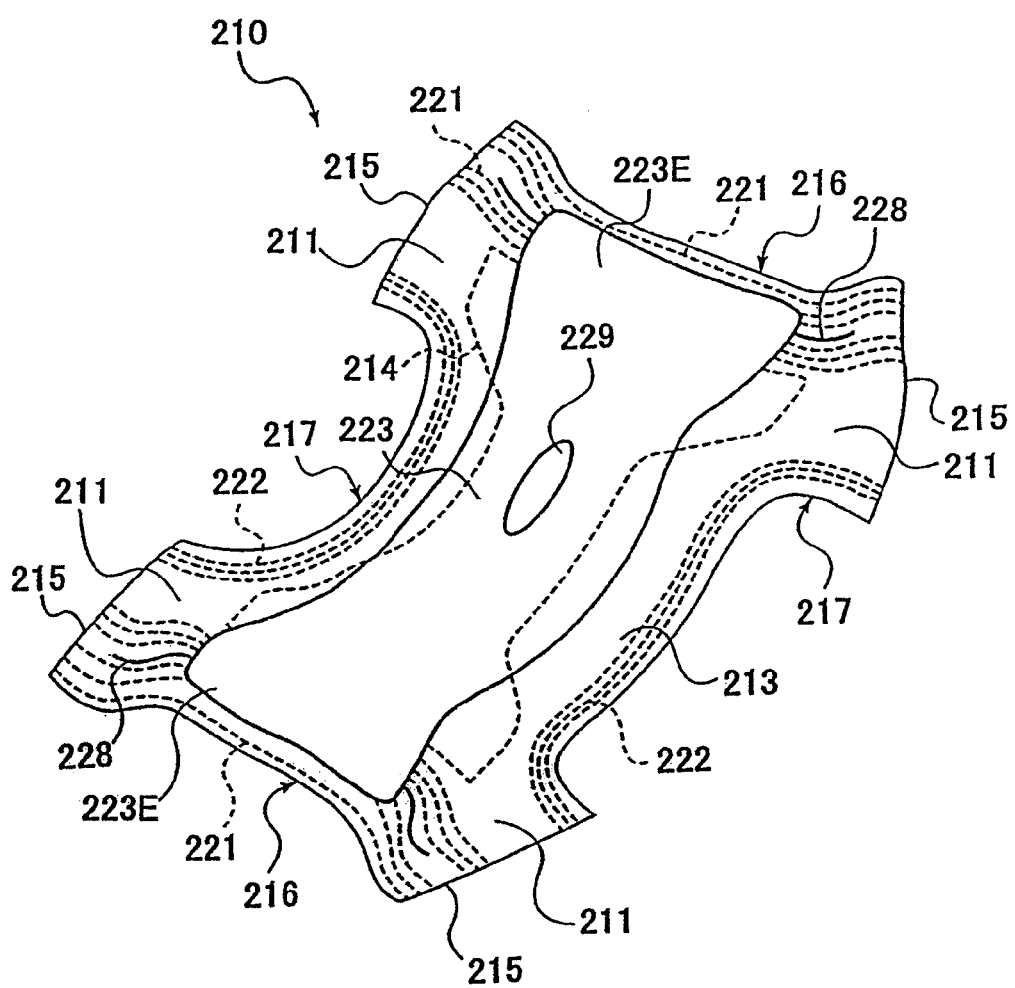
FIG. 30 is a perspective view seen from the inside in a developed state of a different embodiment of the diaper according to the present invention.
Figure 31:
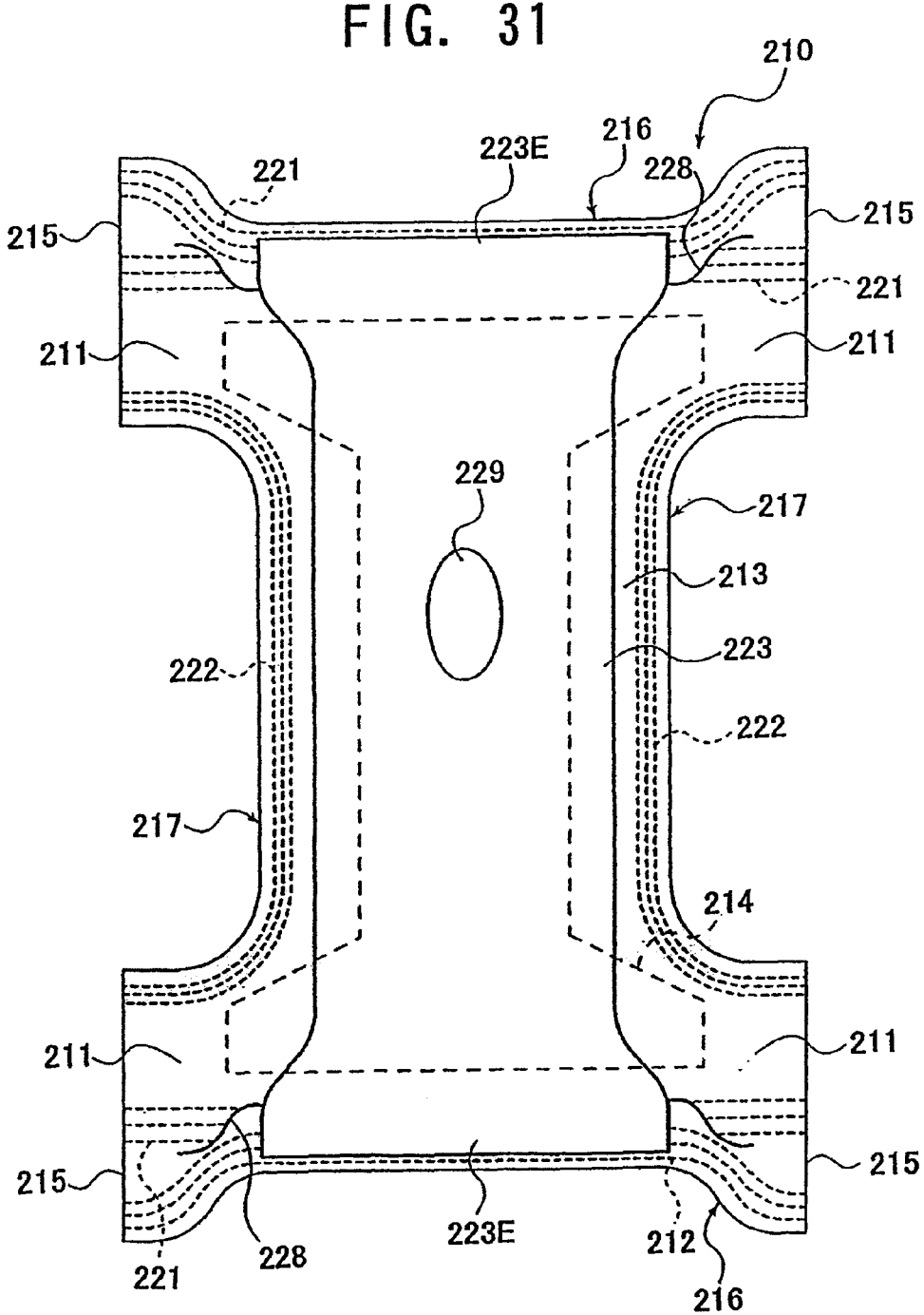
FIG. 31 is a front view of the diaper shown in FIG. 30 on the skin contact sheet side in an extended state on the back sheet side.
Figure 32:
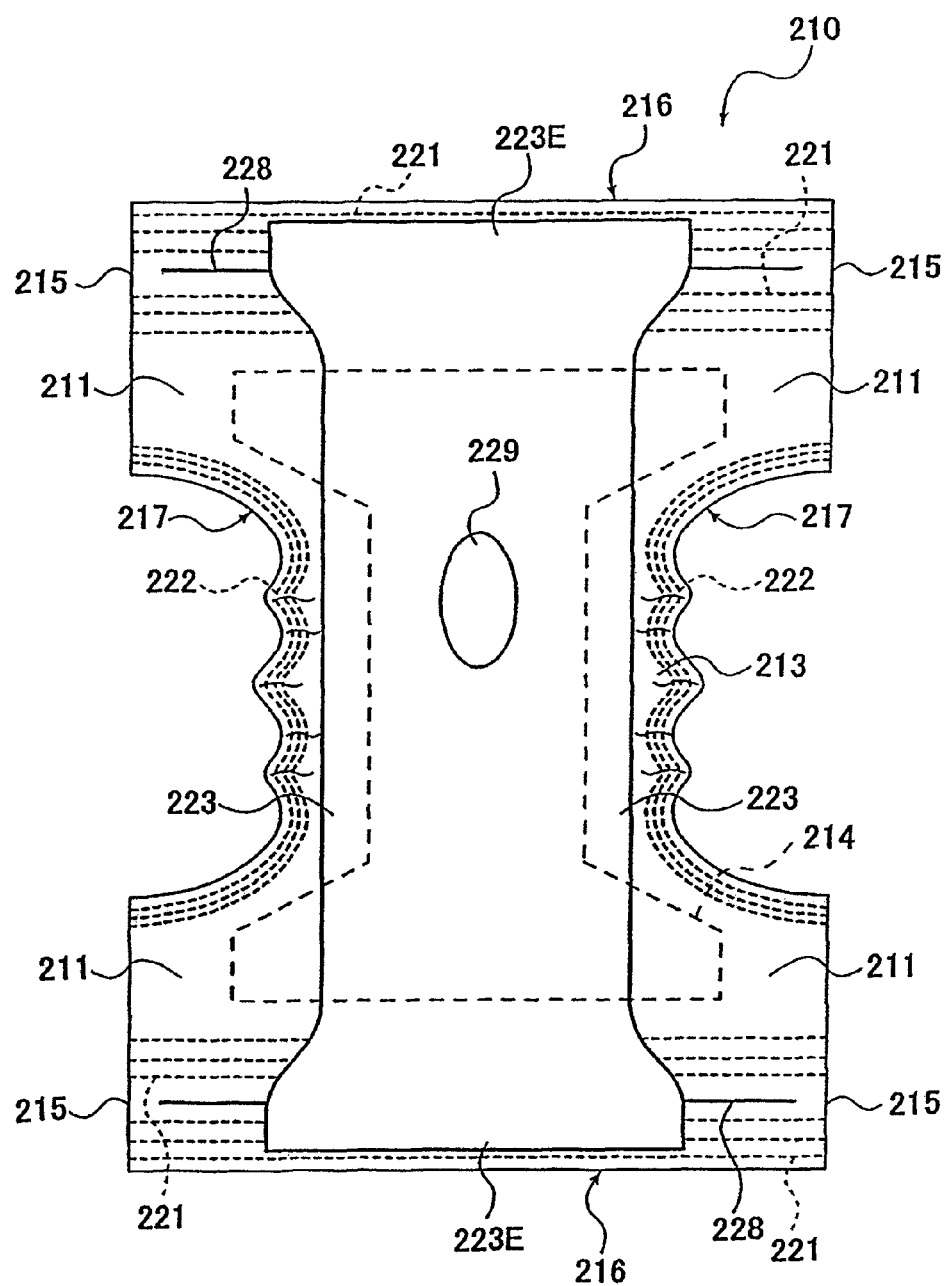
FIG. 32 is a front view of the diaper shown in FIG. 30 on the skin contact sheet side in a non-extended state on the back sheet side.
Figure 33:
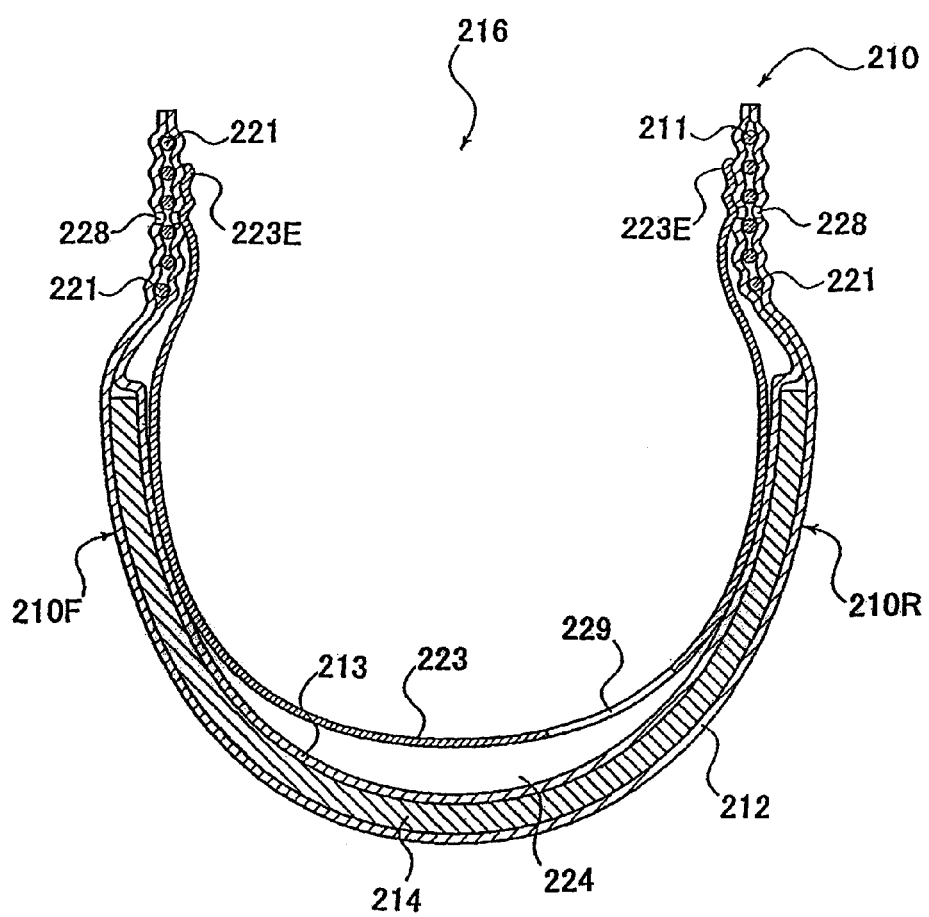
FIG. 33 is a middle sectional view extending to the back body region from the front body region of the diaper shown in FIG. 30.

An appearance of another embodiment of this diaper according to the present invention is shown in FIG. 30 in a developed state, front configurations on the skin contact sheet 223 side are shown in FIGS. 31 and 32 in an extended or non-extended state on the back sheet side, and a middle sectional configuration extending to the back body region from the front body region of the diaper is shown in FIG. 33. The same function members as those of the above embodiment are only denoted with the same reference numerals, and redundant descriptions are omitted.

That is, in the present embodiment the waist surrounding elastic members 221 held between the back sheet 212 and top sheet 213 is divided by the slits 228 reaching the inside and outside of the diaper 210. For the front and back body regions of the diaper 210, the longitudinal-direction opposite ends 223E of the skin contact sheet 223 are joined to the taped waist surrounding opening 216.

Therefore, in the same manner as in the embodiments shown in FIGS. 27 to 29, at the wearing time the tape-shaped portion of the waist surrounding opening 216 is stretched by the skin contact sheet 223 and elongated, and the gap 224 is formed among the skin contact sheet 223, back sheet 212, and top sheet 213.

In the above-described embodiment, the elastic members for the end flaps 220 and waist surrounding elastic members 221 are used to elongate the end flaps 219 and tape-shaped waist surrounding opening 216 at the wearing time, but a stretchable sheet which elongates itself can also be used as the end flap.

Figure 34:
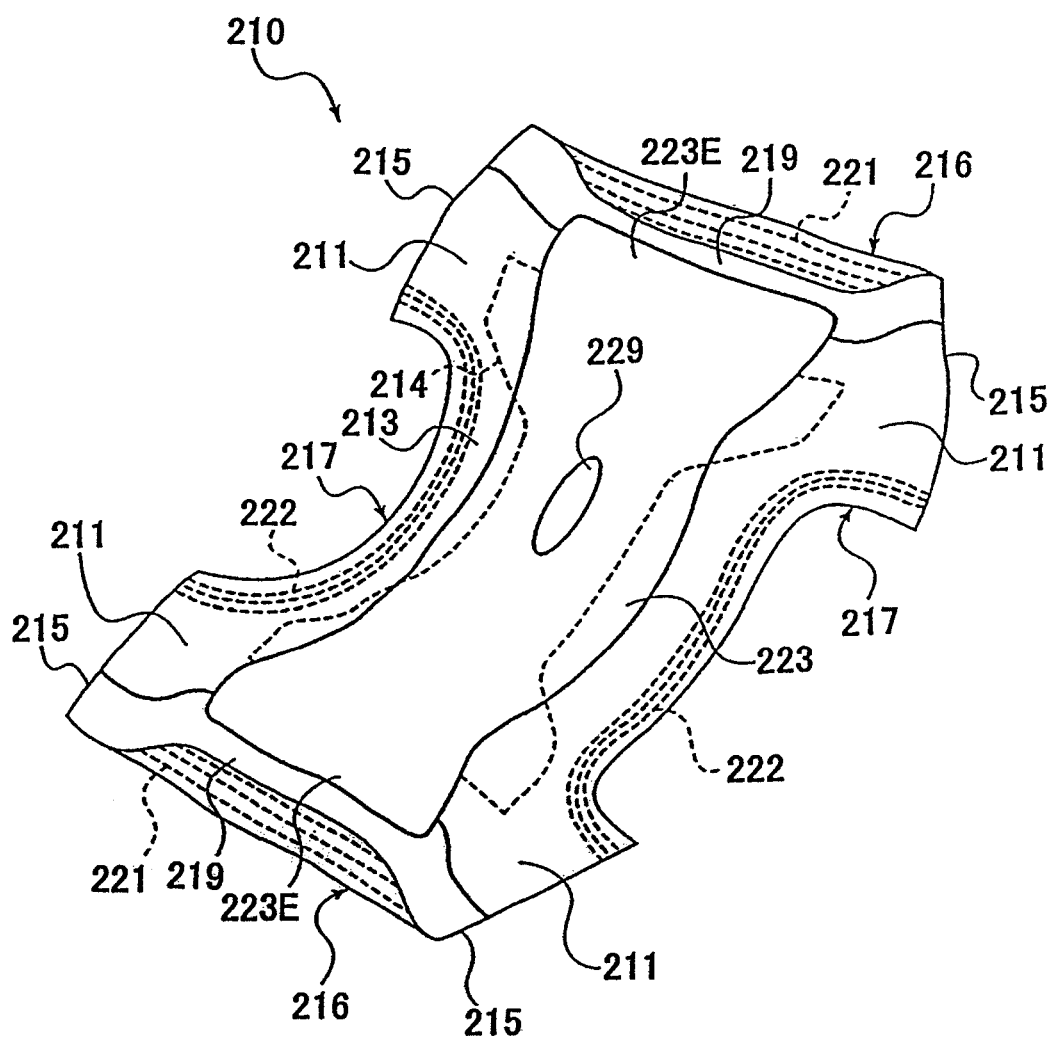
FIG. 34 is a perspective view seen from the inside in a developed state of another embodiment of the diaper according to the present invention.

An appearance of another embodiment of this diaper according to the present invention is shown in FIG. 34 in a developed state, but the same function members as those of the above embodiment are only denoted with the same reference numerals, and redundant descriptions are omitted. That is, the stretchable sheet having stretchable elasticity is used for the end flap 219 in the present embodiment, and disposed along the waist surrounding opening 216, and the opposite ends of the sheet are integrally joined to the joined portion 215. Also in the present embodiment, a longitudinal distance between the portions of the end flaps 219 to which the longitudinal-direction opposite ends 223E of the skin contact sheet 223 are joined is set to be longer than the length of the skin contact sheet 223.

Therefore, at the wearing time the end flaps 219 are stretched by the skin contact sheet 223 and elastically displaced inwards, and a gap is formed among the skin contact sheet 223, back sheet 212, and top sheet 213.

It is to be noted that for use in the stretchable sheet for use as the end flap 219, in addition to a nonwoven cloth having stretchable elasticity, a ribbon-shaped flat rubber of natural rubber, urethane thread, thread rubber, stretchable net, or stretchable film can also be held by the nonwoven cloth, and fixed by measures such as a hot melt adhesive and heat seal.

Figure 35:
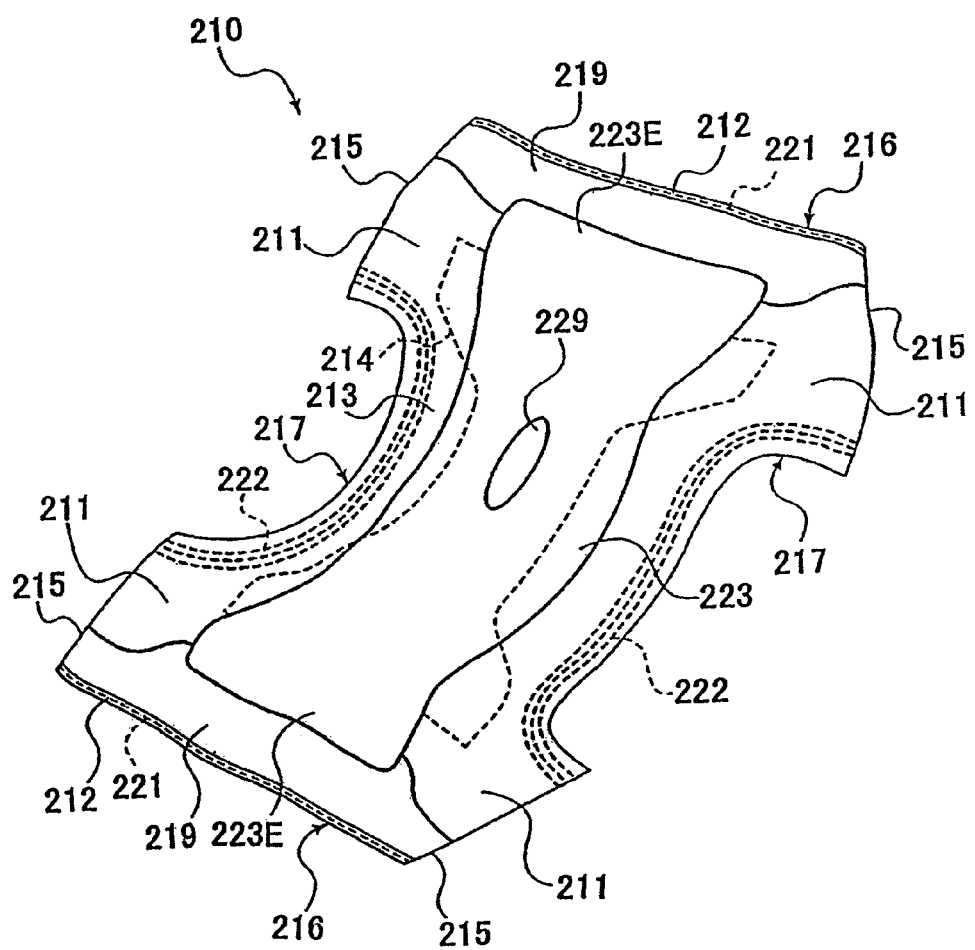
FIG. 35 is a perspective view seen from the inside in a developed state of a still second embodiment of the diaper according to the present invention.

The stretchable sheet can also be joined along the open end of the waist surrounding opening 216, as long as the sheet can elongate along the longitudinal direction of the skin contact sheet 223. An appearance of another embodiment of this diaper according to the present invention is shown in FIG. 35 in a developed state, but the same function members as those of the above embodiment are only denoted with the same reference numerals, and redundant descriptions are omitted. That is, the pair of front and back end flaps 219 to which the longitudinal-direction opposite ends 223E of the skin contact sheet 223 are joined are disposed along the waist surrounding opening 216 using a longitudinally and transversely stretchable sheet, and the open end side of the waist surrounding opening 216 is integrally joined on the top sheet 213. Furthermore, the back sheet 212 is turned back in the joined portion, and the waist surrounding elastic members 221 are held. Therefore, at the wearing time of the diaper 210 the end flaps 219 are stretched by the skin contact sheet 223 to elongate, and the skin contact sheet 223 is in close contact with the wearer's skin.

Figure 36:
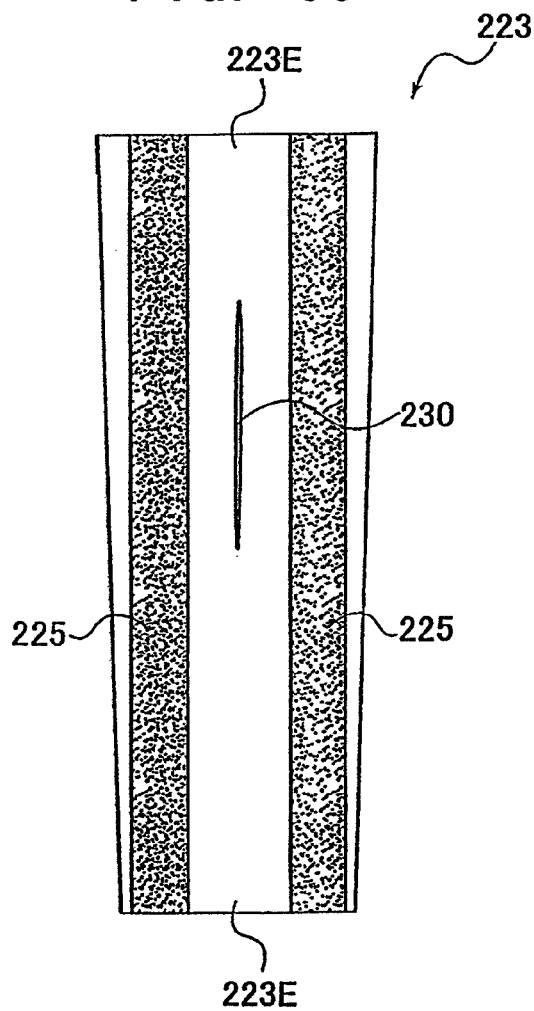
FIG. 36 is a front view of another embodiment of the skin contact sheet for use in the present invention.

In the above-described embodiment, the elliptic opening 229 is formed in the crotch region of the skin contact sheet 223, but the shape of the opening 229 can appropriately be changed, and a cutout portion 230 may have a shape shown in FIG. 36. FIG. 36 shows an appearance of another embodiment of the skin contact sheet 223 according to the present invention. The above-described second absorbers 225 are applied substantially in parallel via the cutout portion 230 along the longitudinal direction of the skin contact sheet 223. When the cutout portion 230 is formed instead of the opening 229, the reverse flow of the stool guided into the gap between the skin contact sheet 223 and top sheet 213 from the cutout portion 230 can be reduced as compared with the above embodiment, and the wearer's backside can be kept to be cleaner.

Figure 37:
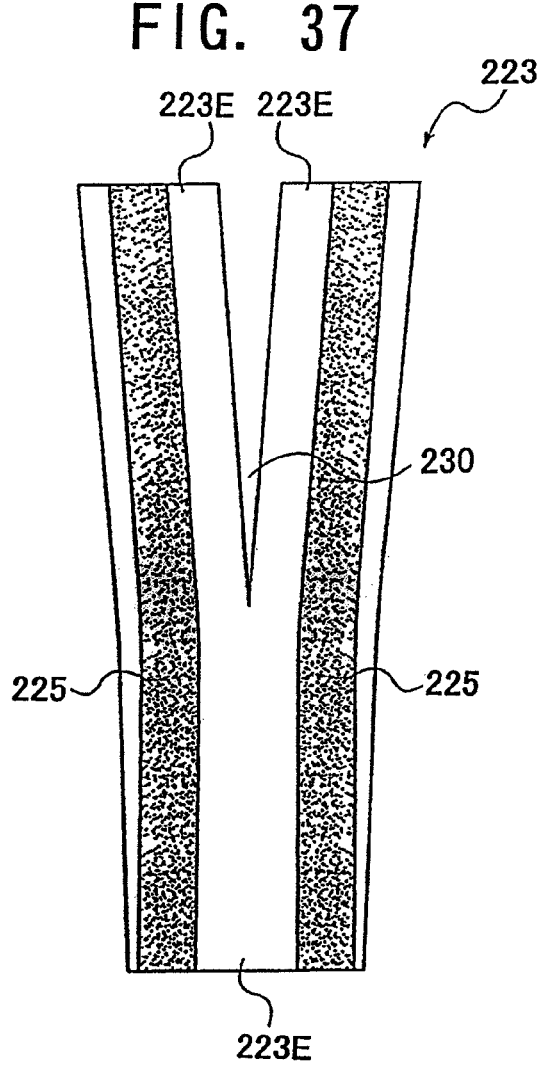
FIG. 37 is a front view of a still second embodiment of the skin contact sheet for use in the present invention.

As shown in FIG. 37, the above-described cutout portion 230 may be disposed over the whole back body region to the longitudinal-direction one end 223, and the interval between the ends is enlarged in a Y shape on the top sheet 213 side. The stool can be guided onto the top sheet 213 through the cutout portion 230.

According to a still another mode (third group) of the present invention, the stretchable band member is formed along at least one waist surrounding opening on the absorber side, the skin contact sheet is disposed on the absorber surface, the stretchable band member is joined to the longitudinal-direction end of the skin contact sheet, and the stretchable property is imparted to the skin contact sheet. At the wearing time of the diaper, the skin contact sheet can constantly be held in a close contact state with respect to the wearer's skin by the contraction force of the stretchable band member stretched by the skin contact sheet.

When the liquid-pervious top sheet is disposed between the absorber and skin contact sheet, the urine is easily absorbed by the absorber. Moreover, even if the wearer's skin is in contact with the top sheet, the skin can be prevented from being directly in contact with the wet absorber.

The end flaps which are disposed along the waist surrounding opening and whose opposite ends are joined onto the absorber side and which have stretchable properties along the waist surrounding opening form the stretchable band member, a pair of front and back end flaps are disposed along the waist surrounding opening, and the longitudinal-direction opposite ends of the skin contact sheet are joined to the pair of end flaps. At least the front body region is formed to be liquid-pervious, the opening is formed in the crotch region, and the length dimension of the skin contact sheet positioned between the pair of end flaps is set to be shorter than the extension dimension between the pair of end flaps. In this case, by the contraction force of the end flap stretched by the skin contact sheet, the skin contact sheet abuts on the wearer in a close contact state, and the gap can be formed between the skin contact sheet and back sheet. Moreover, the stool is guided onto the back sheet through the opening, and the wearer's backside can be isolated from the stool via the skin contact sheet. Even if the sticking range of the stool spreads on the back sheet because of the wearer's movement or stool fluidity after excretion, there can be provided a diaper by which the wearer's backside is not easily soiled and as a result the skin trouble is not easily generated.

When the opening of the skin contact sheet is the cutout portion, the wearer's backside can be kept to be cleaner as a result of suppression of the reverse flow of the stool guided onto the back sheet from the cutout portion.

The end flaps which are disposed along the waist surrounding opening and whose opposite ends are joined onto the absorber side and which have stretchable properties along the waist surrounding opening form the stretchable band members, the pair of front and back end flaps are disposed along the waist surrounding opening, and the longitudinal-direction opposite ends of the skin contact sheet are joined to the pair of end flaps. The cutout portion is formed in the width-direction middle portion of the front body region, the opening is formed in the crotch region and the length dimension of the skin contact sheet positioned between the pair of end flaps is set to be shorter than the extension dimension between the pair of end flaps. In this case, by the contraction force of the end flap stretched by the skin contact sheet, the skin contact sheet abuts on the wearer in a close contact state, and a gap can be formed between the skin contact sheet and back sheet. Moreover, the urine is quickly absorbed by the absorber from the cutout portion of the skin contact sheet, the stool is held onto the back sheet from the opening formed in the skin contact sheet, and, as a result, mixing of these can be prevented.

When at least the back sheet is turned back on the absorber side to form the end flaps, the same material as that of the back sheet can be used as the end flaps. Therefore, it is not necessary to use expensive elastic sheets as the end flaps, and the manufacturing cost of the diaper can be reduced.

When the end flaps include stretchable elastic members disposed along the waist surrounding opening in an extended state, an arbitrary material can be used as the stretchable elastic member as desired. Thereby, abutment strength of the skin contact sheet with respect to the wearer's skin can freely be designed.

The pair of front and back slits are formed along the waist surrounding opening, the stretchable elastic members are disposed along and via the slits in an extended state to form the stretchable band member, and the longitudinal-direction opposite ends of the skin contact sheet are joined in the vicinity of the pair of slits. At least the front body region is formed to the liquid-pervious, the opening is formed in the crotch region, and the length dimension of the skin contact sheet positioned between the pair of slits is set to be shorter than the extension dimension between the pair of slits. In this case, by the contraction force of the stretchable band member stretched by the skin contact sheet, the skin contact sheet abuts on the wearer in a close contact state, and the gap can be formed between the skin contact sheet and back sheet. Moreover, the urine is absorbed by the absorber from the front body region of the skin contact sheet which has a liquid-pervious property, the stool is held onto the back sheet from the opening formed in the skin contact sheet, and, as a result, mixing of these can be prevented.

The pair of front and back slits are formed along the waist surrounding opening, the stretchable elastic members are disposed along and via the slits in an extended state to form the stretchable band member, and the longitudinal-direction opposite ends of the skin contact sheet are joined in the vicinity of the pair of slits. The cutout portion is formed in the width-direction middle portion of the front body region, the opening is formed in the crotch region, and the length dimension of the skin contact sheet positioned between the pair of slits is set to be shorter than the extension dimension between the pair of slits. In this case, by the contraction force of the stretchable band member stretched by the skin contact sheet, the skin contact sheet abuts on the wearer in a close contact state, and a gap can be formed between the skin contact sheet and back sheet. Moreover, the urine is absorbed by the absorber from the cutout portion of the skin contact sheet, the stool is held onto the back sheet from the opening formed in the skin contact sheet, and, as a result, mixing of these can be prevented.

At least one of the longitudinal-direction opposite ends of the skin contact sheet is joined on the open end side of the waist surrounding opening from the slit, or on the crotch region side from the slit. In this case, the stretchable property is improved as compared with the stretchable band member in which the slits are not formed. Therefore, the follow-up property of the skin contact sheet with respect to the wearer's movement can be enhanced.

The stretchable elastic member disposed adjacent to the absorber along the waist surrounding opening is disposed in at least a part of the front and back body regions of the back sheet in an extended state. In this case, the fit property of the diaper around the wearer's waist can be enhanced without unnecessarily deforming the absorber.

To dispose the second absorber in the skin contact sheet, particularly when the second absorber includes a mixture of the super absorbent polymer (SAP) and micro-fibrillated cellulose, and is applied/formed onto the skin contact sheet, dry feeling can be kept even if the wetted skin contact sheet is in contact with the wearer's skin. Additionally, the thickness of the second absorber can be reduced, and the sense of discomfort at the wearing time can be eased.

Moreover, the urine is promptly absorbed by the absorber from the cutout portion of the skin contact sheet through the top sheet, and the stool is held by the skin contact sheet. As a result, mixing of these can be prevented.

INDUSTRIAL APPLICABILITY

According to the present invention, there can be provided an absorbent product in which a skin contact sheet including at least one opening is used to devise a distribution state of openings and arrangements of elastic members and skin troubles such as diaper rash are thereby removed.

What is claimed is:

1. An absorbent product comprising:
 a portion which is constituted of a liquid-impervious back sheet and an absorber superposed upon the back sheet and which extends to a back body portion positioned on a back side from a front body portion positioned on a front side of a wearer in a wearing state,
 wherein a skin contact sheet as an uppermost layer in contact with a wearer's skin is disposed on the absorbent product,
 the skin contact sheet includes at least one opening to allow passage of excretions from the wearer,
 each ends of said skin contact sheet are joined to opposite ends in a longitudinal direction of the absorbent product so that said skin contact sheet is kept in its entirety in a non-contact state with said absorbent product except at longitudinal-direction opposite ends of said skin contact sheet and so that a gap can be formed between said absorbent product and said skin contact sheet, and
 the skin contact sheet is connected to a stretchable band member at the ends of the skin contact sheet in the longitudinal direction, and thereby the skin contact sheet can elastically be displaced with respect to a wearer's body in an appropriate range,
 wherein the stretchable band member includes a pair of front and back slits formed along a waist surrounding opening, and elastic members attached to positions disposed opposite to each other via each slit so as to obtain an extended state in the wearing state, each of the opposite ends of the skin contact sheet in the longitudinal direction is joined to the stretchable elastic band member in the vicinity of each of the pair of slits, and a dimension of the skin contact sheet positioned between the pair of slits in the longitudinal directions is set to be shorter than an extension dimension between the pair of slits.

2. The absorbent product according to claim 1, wherein a cutout portion is formed in the middle portion of the front body region of the skin contact sheet in the width direction, and an opening is formed in a crotch region.

3. The absorbent product according to claim 1, wherein at least one of opposite ends of the skin contact sheet in the longitudinal direction is joined to the stretchable band member on a side of the slit close to an opening end of the waist surrounding opening, or on a side close to a crotch region from the slit.

* * * * *